Figure 1:
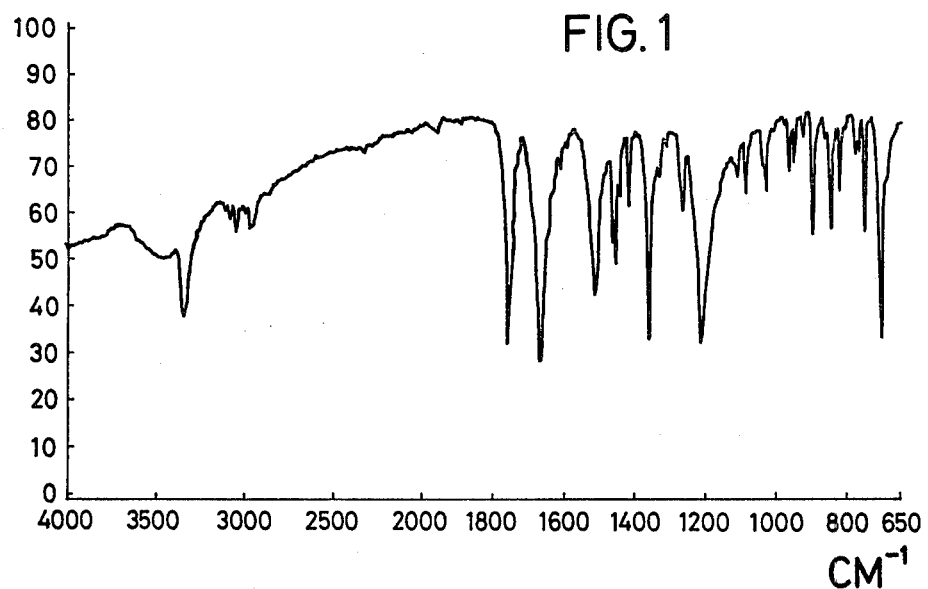

United States Patent [19]

Nakamizo et al.

[11] 4,138,485

[45] Feb. 6, 1979

[54] PHENYLALANINE DERIVATIVES

[75] Inventors: Nobuhiro Nakamizo; Masayuki Teranishi; Ikuo Matsukuma, all of Machida; Katsuichi Shuto; Koji Yamada, both of Shizuoka, all of Japan

[73] Assignee: Kyowa Hakko Kogyo Kabushiki Kaisha, Ohte, Japan

[21] Appl. No.: 771,726

[22] Filed: Feb. 24, 1977

[30] Foreign Application Priority Data

Feb. 25, 1976 [JP] Japan .................................. 51-18871
Feb. 25, 1976 [JP] Japan .................................. 51-18872
Jun. 18, 1976 [JP] Japan .................................. 51-70958
Nov. 24, 1976 [JP] Japan .................................. 51-140949

[51] Int. Cl.$^2$ ................. A61K 31/535; C07C 153/11; C07D 211/06; A61K 31/27
[52] U.S. Cl. ..................... 424/248.5; 260/455 A; 544/159; 424/300; 424/267; 546/205; 546/206; 546/226
[58] Field of Search ...................... 260/455 A, 293.73; 544/159; 424/300, 267, 248.5

[56] References Cited

U.S. PATENT DOCUMENTS

| | | | |
|---|---|---|---|
| 2,863,899 | 12/1958 | Harris | 260/455 A |
| 3,742,005 | 6/1973 | Tilles | 260/455 A |
| 3,954,729 | | Sato et al. | 260/455 A |

OTHER PUBLICATIONS

Morrison and Boyd, "Organic Chemistry", 2nd Edition, Allyn and Bacon, Inc., 1966, pp. 671 and 673.
Kollonitsch et al., Chemische Berichte, vol. 89, p. 2293, (1956).
Siemion et al., Chemical Abstracts, vol. 74, 23116J, (1971).

*Primary Examiner*—Elbert L. Roberts
*Assistant Examiner*—Robert C. Whittenbaugh
*Attorney, Agent, or Firm*—Wolder, Gross & Yavner

[57] ABSTRACT

This invention relates to certain derivatives of phenylalanine having interesting pharmaceutical properties, in particular, a lipid-lowering activity.

15 Claims, 20 Drawing Figures

PHENYLALANINE DERIVATIVES

Although various lipid-lowering agents are known, it is generally found that the lipid-lowering agents such as cholesterol lowering agents conventionally used have a rather high toxicity and often induce various side effects such as for example liver lesion. There is thus a need for lipid-lowering agents having a low toxicity and no undesired side effects.

Certain derivatives of phenylalanine such as benzyl-thiocarbonal phenylalanine [Chemische Derichte, Vol. 89, page 2293 (1956) and Nature, Vol. 177, page 841 (1956) and N-benzylcarbonyl phenylalanine ethylester [Chemical Abstract, Vol. 74, 23116 J (1971)] are previously known, although it was not known in the art that these compounds had lipid-lowering activity.

It has unexpectedly been discovered that certain derivatives of phenylalanine show lipid-lowering activity, viz. compounds of the general formula:

(I)

[wherein A is a phenyl group, a substituted phenyl group, a naphthyl group or a substituted naphthyl group, and R is a hydroxy group, an alkoxy group, an amino group or a substituted amino group], and pharmaceutically acceptable salts thereof.

As a result of various experiments as hereinafter described, it has been found that the compounds of the formula (I) as hereinbefore defined show, in general, a cholesterol-lowering activity and some of these compounds are furthermore capable of lowering other lipids such as triglyceride.

Thus the present invention provides a pharmaceutical composition comprising as active ingredient a compound of the formula (I) as hereinbefore defined or a pharmaceutically acceptable salt thereof, in association with a pharmaceutical carrier or excipient.

According to the invention, the phenyl or naphthyl group of A in the formula (I) are substituted with 1 to 5 groups selected from an alkyl group having carbon atoms of 1 to 5 (e.g. 2-methyl, 3-methyl, 4-methyl, 2,5-dimethyl, 2,6-dimethyl, 3,4-dimethyl, 2,3,4-trimethyl, 2,3,4,5,6-pentamethyl, 4-ethyl, 4-n-butyl, or 4-tert-butyl group), an alkoxy group having carbon atoms of 1 to 4 (e.g. 2-methoxy, 4-methoxy, or 2,3-dimethoxy group), a halogen atom (e.g. 2-fluoro, 3-fluoro, 4-fluoro, 2-chloro, 3-chloro, 4-chloro or 4-bromo atom), 3-chloro-4-methoxy or 4-methoxy-3,5-dichloro group, a hydroxy group (e.g. 4-hydroxy group), an acetoxy group (e.g. 4-acetoxy group) and/or a nitro group (e.g. 2-nitro or 4-nitro group).

The alkoxy group of R has carbon atoms of from 1 to 6 (e.g. methoxy, ethoxy, n-propoxy, iso-propoxy, n-butoxy, t-butoxy or n-hexyloxy group) and the substituted amino group of R has carbon atoms of 1 to 12 (e.g. methylamino, ethylamino, butylamino, cyclohexylamino, dimethylamino, diethylamino, dicyclohexylamino, piperidino or morpholino group).

Beside benzylthiocarbonyl phenylalanine and N-benzylthiocarbonyl phenylalanine ethylester as set forth, the compounds of the formula (I) as hereinbefore defined are new compounds. Thus, the other compounds, viz. compounds of the formula (I) [wherein (a) A is a substituted phenyl group, a naphthyl group or a substituted naphthyl group, and R is a hydroxy group, an alkoxy group, an amino group or a substituted amino group; or (b) A is a phenyl group and R is an amino group, a substituted amino group or a methoxy group] are new compounds which constitute a further feature of the present invention.

The compounds having lipid-lowering properties according to the present invention may be produced by various processes exemplified by the following description. According to the above-mentioned report [Chemische Berichte and Nature], benzylthiocarbonyl phenylalanine ester is synthesized from benzylthiocarbonyl chloride and phenylalanine ester, and is then hydrolized to form benzylthiocarbonyl phenylalanine. Basically, most compounds of the phenylalanine derivatives of the formula (I) may be produced by application of this known knowledge viz. compounds of the following formulae:

(I')

[wherein A' is a phenyl group, a substituted phenyl group, a naphthyl group or a substituted naphthyl group. In this case, the phenyl or naphthyl group may be substituted with 1 to 5 groups selected from an alkoxy group having carbon atoms of 1 to 4, an alkyl group having carbon atoms of 1 to 5 an acetoxy group, a halogen atom or a nitro group. R is as hereinbefore defined.] and

(I'')

[wherein A'' is a phenyl group, a substituted phenyl group, a naphthyl group or a substituted napthyl group. In this case, the phenyl group or naphthyl group may be substituted with 1 to 5 groups selected from an alkyl group having carbon atoms of 1 to 5, an alkoxy group having carbon atoms of 1 to 5, a halogen atom or a nitro group], both belonging to the compounds of the formula (I) as hereinbefore defined. Also it is obvious that the compounds of the following formula:

(I''')

[wherein A'' is as hereinbefore defined and R' is an alkoxy group having carbon atoms of 1 to 6] used as the starting compound for the production of the compound (I'') as hereinbefore defined may be obtained by producing the compounds (I') as hereinbefore defined.

On the other hand, the process described has the disadvantage that phosgene, a poisonous gas is used to produce benzylthiocarbonyl chloride. In order to overcome this disadvantage, it has been found that the compounds of the formula (I') are produced by the use of phenylalanine or derivatives thereof of the formula:

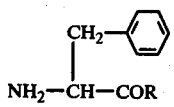  (II)

[wherein R is as hereinbefore defined], carbonyl sulfide and a halomethyl compound of the formula: ]

  (III)

[wherein A' is as hereinbefore defined and X is a halogen atom].

When compared with the known process, this process has the advantage that benzylthiocarbonyl phenylalanine is produced in a simple manner by the use of benzylchloride and carbonyl sulfide. Also it has been found that the compounds of the formula (I) [wherein A is a phenyl group substituted with a hydroxy group and R is an alkoxy group having carbon atoms of 1 to 6] are produced, for example, by simultaneously hydrolyzing and esterifying the compounds of the formula (I″) having an acetoxy group as a substituent.

Thus the present invention is further directed to provide processes for producing the compounds of the formula (I) as hereinbefore defined.

(A) Production of the compounds (I'):
In the process, the reaction proceeds as follows.

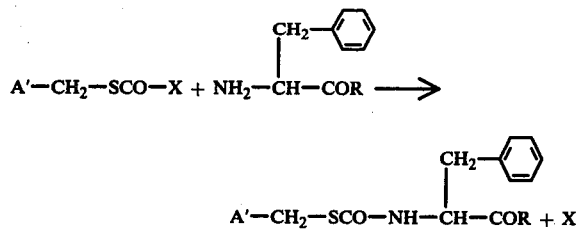

[wherein A', R and X are as hereinbefore defined]

More clearly, phenylalanine or a derivative thereof of the formula:

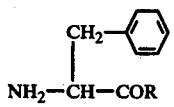  (II)

[wherein R is as hereinbefore defined] is suspended or dissolved in water, an organic solvent or a mixture thereof, and is subjected to the reaction with a thiocarbonyl halide of the formula:

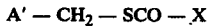  (IV)

[wherein A' and X are as hereinbefore defined] to obtain the desired compounds of the formula (I') as hereinbefore defined.

The reaction is usually carried out at a temperature of from −50° to 50° C. (preferably from −5° to 25° C.) in the presence or absence of a base. The concentration of phenylalanine or a derivative thereof is usually from 0.01 to 3 mol per one litre of the used solvent to complete the reaction within a range of from 30 minutes to 3 hours.

Phenylalanine or derivatives thereof which may be used for this process is either in the free form or in the form of an acid addition salt which may be formed with inorganic acids such as e.g. hydrochloric acid, hydrobromic acid and like, or with organic acids such as e.g. acetic acid, trifluoroacetic acid and like. When an acid addition salt is used, it is preferred to add a base to the reaction system.

The type of the derivatives of phenylalanine used for this process are selected, depending upon the types of the desired compounds.

Preferable derivatives of phenylalanine used for this process include e.g. methylester, ethylester, n-propylester, isopropylester, n-butylester, t-butylester or n-hexylester of phenylalanine; amide, methylamide, ethylamide, n-butylamide, cyclohexylamide, dimethylamide, diethylamide or dicyclohexylamide of phenylalanine; phenylalanine piperidide and phenylalanine morpholide. These derivatives may be optically active or inactive.

Solvents which are used for this process are water and organic solvents which do not react with the reaction materials. Preferable inert solvents are exemplified by various aromatic hydrocarbons such as benzene, toluene and xylene; halogenated hydrocarbons such as methylene chloride, chloroform, dichloroethane and carbon tetrachloride; esters such as methyl acetate and ethyl acetate; ethers such as diethylether, dioxane and tetrahydrofuran; ketones such as acetone, methylethyl ketone and diethyl ketone; acetonitrile and dimethylformamide. These organic solvents may be used solely or in combination of two or more solvents. When the solvent is mixed with water, the amount of the solvent is preferably from ¼ to 4 times the volume of water.

Bases used for this process are inorganic or organic bases. Organic bases which may preferably used are for example sodium hydroxide, potassium hydroxide, sodium carbonate, potassium carbonate and sodium bicarbonate; and organic bases are exemplified by triethylamine, N-methylmorpheline, dimethyl aniline and pyridine. It is also possible to use the phenylalanine or its derivative as the base when the free amino group is present in the phenylalanine or its derivative used as starting material.

It is preferred to add to the reaction system the thiocarbonyl halide excessively by an amount of from 0.05 to 1 mol per one mol of phenylalanine or its derivative. The base is preferably used excessively by an amount of from 0.05 to 1 mol per one mol of thiocaronyl halide. When phenylalanine or its derivaive is used in the form of acid addition salt, it is necessary for converting the salt into its free form to use additionally an equimolar amount of the base per one mol of the acid addition salt. When phenylalanine or its derivative used as a starting material has a carboxyl group, it is further necessary to use an equimolar amount of the base which will be consumed by the carboxyl group.

The desired compound may be isolated from the reaction solution and purified in conventional manner used in the field of the organic synthesis.

(B) Production of the compounds (I″):
A derivative of phenylalanine which may be produced by process A, described previous and which has the following formula is used for this process.

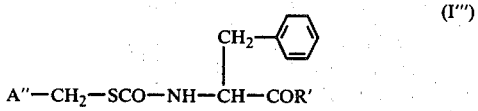  (I''')

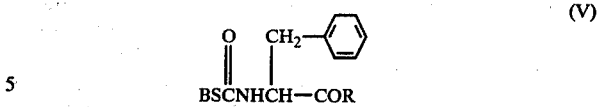  (V)

[wherein A'' and R' are as hereinbefore defined]

The compounds (I''') as set forth may also be produced by Process C as hereinafter described.

The starting compound (I''') is hydrolyzed by heating in a solvent in the presence of an acid catalyst to obtain the desired compound of the formula:

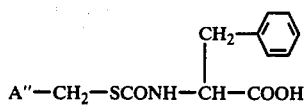  (I'')

[wherein A'' is as hereinbefore defined].

Acid catalysts which may be used for this process are inorganic acids such as for example hydrochloric acid, hydrobromic acid, hydroiodic acid and like; and organic acids such as for example formic acid, acetic acid, propionic acid, p-toluene sulfonic acid and like. It is also possible to use these acids as the reaction solvents if desired. However, a suitable organic solvent may also be used when it is inert. Solvents which may be preferably used for this process are for example benzene, toluene, xylene and dioxane.

The reaction is usually carried out at a concentration of from 0.01 to 1 mol per one litre of the total solvent at a temperature of from 50° to 180° C. (preferably from 100° to 150° C.) for a period of from 15 minutes to 3 hours.

The desired compound may be isolated from the reaction solution and purified in conventional manner used in the field of the organic synthesis.

(C) Production of the compounds (I'):

In this process the reaction proceeds as follows.

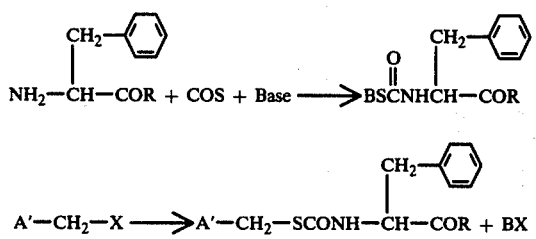

[wherein A', R and X are as hereinbefore defined; B is an alkali metallic ion of an inorganic base or an ammonium ion of an organic base; and Base is an inorganic or organic base]

More clearly, phenylalanine or a derivative thereof of the formula:

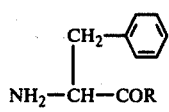  (II)

[wherein R is as hereinbefore defined] is subjected to the reaction with carbonyl sulfide in a solvent in the presence of a base to form a salt of thiolcarbamic acid of the formula:

[wherein B and R are as hereinbefore defined], which is then subjected to the reaction with a halomethyl compound of the formula:

A' - CH$_2$ - X   (III)

[wherein A' and X are as hereinbefore defined] to obtain the desired compound of the formula:

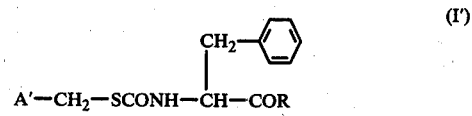  (I')

[wherein A' and R are as hereinbefore defined].

The reaction is usually effected with agitation at a temperature below 50° C., preferably from −5° C. to 20° C. by feeding carbonyl sulfide into the solvent containing phenylalanine or its derivative as the starting material and a base to form a salt of thiolcarbamic acid as intermediate, followed by the reaction of the salt with a halomethyl compound at a temperature of from 0° to 50° C. The reaction proceeds instantly by the addition of the halomethyl compound, while the agitation is preferably continued for 30 minutes to 3 hours for completion of the reaction.

The salt of thiolcarbamic acid formed in the first step may, if desired, be transferred to the second step without being isolated from the reaction solution.

The organic solvents, bases and phenylalanine or derivatives thereof used for this process are analogous to those used in the above-mentioned Process A, otherwise specified.

Halomethyl compounds used for this process are selected, depending upon the types of the desired compounds, from benzylhalide, substituted benzyl halide or halomethylnaphthalene.

Preferable halomethyl compounds for this process are exemplified by benzylchloride, benzylbromide, 1-(chloromethyl)-naphthalene, 1-(bromomethyl)-naphthalene, 2-(chloromethyl)-naphthalene and 2-(bromomethyl)-naphthalane. It is also possible to use benzylchloride or benzylbromide having a phenyl group substituted for example with 2-methyl; 3-methyl; 4-methyl; 2,5-dimethyl; 2,6-dimethyl; 3,4-dimethyl; 2,3,4-trimethyl; 2,3,4,5,6-pentamethyl; 4-ethyl; 4-n-butyl; 4-tert-butyl; 2-methoxy, 4-metoxy; 2,3-dimethoxy; 4-acetoxy; 2-fluoro, 3-fluoro; 4-fluoro; 2chloro; 3-chloro; 4-chloro; 4-bromo; 3-chloro-4-methoxy; 4-methoxy-3,5-dichloro; 2-nitro or 4-nitro group.

It is preferred for preparing the desired compound with a good yield to use carbonyl sulfide in an equimolar amount or less (for example, from 1 to 0.8 mol) per one mol of the used phenylalanine or its derivative.

It is necessary for forming the salt of thiolcarbamic acid of the starting material to use the base in an equimolar amount per one mol of the used phenylalanine or its derivative. However, when phenylalanine or its derivative is used in the form of an acid addition salt, it is necessary for converting the amino group into the free form to use a further equimolar amount of the base per one mol of the starting material. When phenylalanine itself is used as the starting material, it is also necessary for converting the carboxyl group into the salt form to use additionally an equimolar amount of the base.

Although the mol ratio of the salt of thiolcarbamic acid to the halomethyl compound may be around 1:1, it is preferred for preparing the desired compound with a good yield to use a more or less excessive amount of the former within an economically acceptable range.

The desired compound may be isolated from the reaction solution and purified in conventional manner used in the field of the organic synthesis.

(D) Production of the compounds (I'''):

A derivative of phenylalanine which may be produced by Process A or C of the formula (I'') [wherein A'' is as hereinbefore defined] is esterified by the reaction with an alcohol of the formula: R'H [wherein R' is as hereinbefore defined] in the presence of an acid catalyst to obtain the desired compound of the formula:

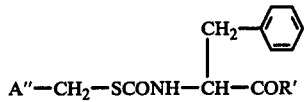

A''—CH$_2$—SCONH—CH—COR'  (I''')

[wherein A'' and R' are as hereinbefore defined].

Acid catalysts which may be preferably used for this process are for example thionyl chloride and hydrogen chloride. Alcohols used for this process are one having carbon atoms of from 1 to 6 (e.g. methanol, ethanol, n-butanol, t-butanol and n-hexanol). It is possile if desired to use such alcohol as the reaction solvent, although it is also possible to use suitable organic solvents which may be used for the alreadymentioned processes.

The reaction is usually carried out at a temperature of from −5° to 30° C for a period of from about 2 to 24 hours.

The isolation and purification of the desired compound may be carried out in conventional manner used in the field of the organic synthesis.

It is also possible to modify this process such that A'' of the starting compound (I'') has an acetoxy group as a substituent, resulting in a desired compound (I''') having a hydroxy group as a substituent, as is described in the undergoing Example 11.

(E) Production of the compound of the formula (I) wherein A is an OH-substituted phenyl group:

It is also possible to modify Process B to produce a compound of the formula:

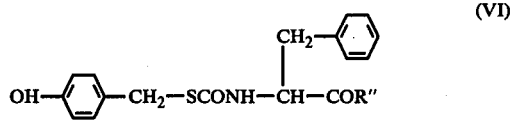

OH—⟨⟩—CH$_2$—SCONH—CH—COR''  (VI)

[wherein R'' is a hydroxy group, an amino group or a substituted amino group as hereinbefore defined], in which a compound of the formula:

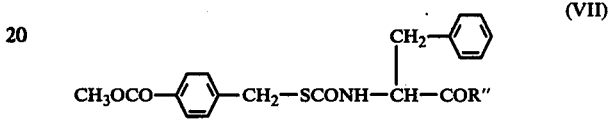

CH$_3$OCO—⟨⟩—CH$_2$—SCONH—CH—COR''  (VII)

[wherein R'' is as hereinbefore defined] to effect the hydrolysis of the acetoxy group in usual manner at a temperature of −5° to 50° C.

It is obvious that the compounds having a lipid-lowering activity according to the present invention may be produced by the processes described above.

The pharmaceutically acceptable salts according to the present invention may be obtained from these compounds in conventional manner used in the field of the oganic synthesis. These salts are exemplified by those formed with sodium, potassium, lithium, ammonium, calcium, barium, lysine, triethylamine, dimethylamine and like.

The compounds of the formula (I) according to the present invention which may be produced by the above-mentioned processes are exemplified in Table 1. Compound numbers in this table will be referred to hereinafter.

Table 1

| Compound No. | Name of Compound | Definition of A and R in General Formula(I) | | Optical Rotation $[\alpha]_D^{26*}$ | Melting Point (° C) | Remarks |
|---|---|---|---|---|---|---|
| | | A | R | | | |
| 1 | N-(4-methylbenzylthiocarbonyl)-L-phenylalanine | CH$_3$—⟨⟩— | —OH | +35.9 | 92–93 | Example 3 |
| 2 | N-(4-methylbenzylthiocarbonyl)-L-phenylalanine methylester | CH$_3$—⟨⟩— | —OCH$_3$ | +9.1 | 84–86 | Example 8 |
| 3 | N-(4-methylbenzylthiocarbonyl)-L-phenylalanine ethylester | CH$_3$—⟨⟩— | —OC$_2$H$_5$ | +11.4 | 37–39 | Synthesis acc. Example 8 |
| 4 | N-(4-methylbenzylthiocarbonyl)-L-phenylalanine amide | CH$_3$—⟨⟩— | —NH$_2$ | −1.5 | 158–158.5 | '' |
| 5 | N-(4-methylbenzylthiocarbonyl)-L-phenylalanine ethylamide | CH$_3$—⟨⟩— | —NHC$_2$H$_5$ | −9.5 | 138–140 | '' |
| 6 | N-(4-methylbenzylthiocarbonyl)-L-phenylalanyl-L-phenylalanine methylester | CH$_3$—⟨⟩— | —NH—CH(CH$_2$—⟨⟩)—COOCH$_3$ | +14.6 | 115–117 | Example 10 |
| 7 | N-(4-chlorobenzylthiocarbonyl)-L-phenylalanine | Cl—⟨⟩— | —OH | $[\alpha]_D^{20}$ +28.3 | 101–103 | Example 9 |
| 8 | N-(4-chlorobenzylthiocarbonyl)-L-phenylalanine methylester | Cl—⟨⟩— | OCH$_3$ | +4.6 | 71–73 | Synthesis acc. to Example 6 |

Table 1-continued

| Compound No. | Name of Compound | Definition of A and R in General Formula(I) A | R | Optical Rotation $[\alpha]_D^{26*}$ | Melting Point (° C) | Remarks |
|---|---|---|---|---|---|---|
| 9 | N-(4-chlorobenzylthiocarbonyl)-L-phenylalanine amide |  | —NH$_2$ | — | 165–166 | Synthesis acc. to Example 6 |
| 10 | N-(4-chlorobenzylthiocarbonyl)-L-phenylalanine ethylamide |  | —NHC$_2$H$_5$ | −10.8 | 158.5–159.5 | Example 4 |
| 11 | N-(4-chlorobenzylthiocarbonyl)-L-phenylalanyl-L-phenylalanine methylester |  |  | +14.4 | 143–144.5 | Synthesis acc. to Example 10 |
| 12 | N-(4-fluorobenzylthiocarbonyl)-L-phenylalanine methylester |  | —OCH$_3$ | $[\alpha]_D^{20}$ +6.6 | 66–68 | " |
| 13 | N-(4-methoxybenzylthiocarbonyl)-L-phenylalanine methylester |  | —OCH$_3$ | +8.5 | 91.5–93 | Synthesis acc. to Example 6 |
| 14 | N-(4-nitrobenzylthiocarbonyl)-L-phenylalanine |  | —OH | +26.4 | 149–150 | Example 5 |
| 15 | N-(4-nitrobenzylthiocarbonyl)-L-phenylalanine methylester |  | —OCH$_3$ | +0.8 | 78–81 | Synthesis acc. to Example 6 |
| 16 | N-benzylthiocarbonyl-L-phenylalanine |  | —OH | +34.0 | 63–65 | Example 1 |
| 17 | N-benzylthiocarbonyl-D,L-phenylalanine |  | —OH | — | 101–103 | Synthesis acc. to Example 3 |
| 18 | N-benzylthiocarbonyl-L-phenylalanine methylester |  | —OCH$_3$ | +8.0 | 46–47 | Example 2 |
| 19 | N-benzylthiocarbonyl-D,L-phenylalanine methylester |  | —OCH$_3$ | — | 82.4–84 | Synthesis acc. to Example 6 |
| 20 | N-(2-methylbenzylthiocarbonyl)-L-phenylalanine |  | —OH | +30.0 | 94–95.5 | Synthesis acc. to Example 3 |
| 21 | N-(2-methylbenzylthiocarbonyl)-L-phenylalanine methylester |  | —OCH$_3$ | +7.0 | 50–53 | Synthesis acc. to Example 6 |
| 22 | N-(3-methylbenzylthiocarbonyl)-L-phenylalanine |  | —OH | +35.4 | 90–92 | Synthesis acc. to Example 3 |
| 23 | N-(3-methylbenzylthiocarbonyl)-L-phenylalanine methylester |  | —OCH$_3$ | +9.5 | 41–42.5 | Synthesis acc. to Example 6 |
| 24 | N-(2,6-dimethylbenzylthiocarbonyl)-L-phenylalanine |  | —OH | +17.0 | 103–106 | Synthesis acc. to Example 7 |
| 25 | N-(2,6-dimethylbenzylthiocarbonyl)-L-phenylalanine methylester |  | —OCH$_3$ | −3.8 | 128–129 | Synthesis acc. to Example 6 |
| 26 | N-(2,5-dimethylbenzylthiocarbonyl)-L-phenylalanine |  | —OH | +31.0 | 92–94 | Synthesis acc. to Example 7 |
| 27 | N-(2,5-dimethylbenzylthiocarbonyl)-L-phenylalanine |  | —OCH$_3$ | +7.2 | 63.5–64 | Example 6 |
| 28 | N-(4-tert-butylbenzylthiocarbonyl)-L-phenylalanine |  | —OH | +31.2 | 48–51 | Synthesis acc. to Example 7 |

Table 1-continued

| Compound No. | Name of Compound | Definition of A and R in General Formula(I) A | R | Optical Rotation $[\alpha]_D^{26*}$ | Melting Point (° C) | Remarks |
|---|---|---|---|---|---|---|
| 29 | N-(2,3,4,5,6-pentamethylbenzyl-thiocarbonyl)-L-phenylalanine | 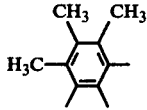 | —OH | +14.0 | 202–203 | Synthesis acc. to Example 7 |
| 30 | N-(2,3,4,5,6-pentamethylbenzyl-thiocarbonyl)-L-phenylalanine methylester | 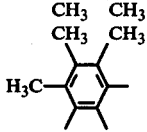 | —OCH$_3$ | −4.0 | 114–115 | Synthesis acc. to Example 6 |
| 31 | N-(α-naphthylmethylthiocarbonyl)-L-phenylalanine |  | —OH | +26.9 | 130–132 | Example 7 |
| 32 | N-(α-naphthylmethylthiocarbonyl)-L-phenylalanine methylester |  | —OCH$_3$ | +3.1 | 71–72.5 | Synthesis acc. to Example 6 |
| 33 | N-(4-fluorobenzylthiocarbonyl)-L-phenylalanine |  | —OH | +30.2 | 64–66 | Synthesis acc. to Example 3 |
| 34 | N-(4-methylbenzylthiocarbonyl)-D-phenylalanine |  | —OH | −36.1 | 92–93.5 | " |
| 35 | N-(4-methylbenzylthiocarbonyl)-DL-phenylalanine |  | —OH | — | 120.5–122 | " |
| 36 | N-(4-acetoxybenzylthiocarbonyl)-L-phenylalanine | 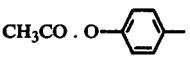 | —OH | +26.7 | 87–89 | " |
| 37 | N-(4-hydroxybenzylthiocarbonyl)-L-phenylalanine methylester |  | —OCH$_3$ | +6.1 | 113.5–114.5 | Example 11 |

Note: *Optical Rotation $[\alpha]_D^{26}$ (C = 1 in ethyl acetate) Nos. 7 & 12 —$[\alpha]_D^{20}$
—: not measured The IR spectrum (KBr tablet) and NMR spectrum of these compounds are shown in the accompanying drawings as follows. IR spectrum —

FIG. 1: N-benzylthiocarbonyl-L-phenylalanine methylester (Compound No. 18)

Figure 2:
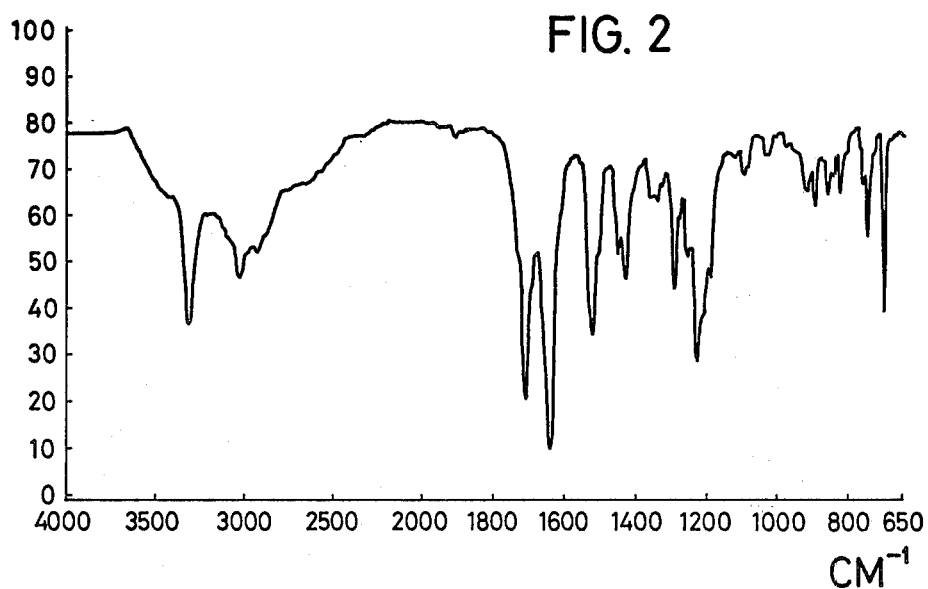

FIG. 2: N-(4-methylbenzylthiocarbonyl)-L-phenylalanine (Compound No. 1)

Figure 3:
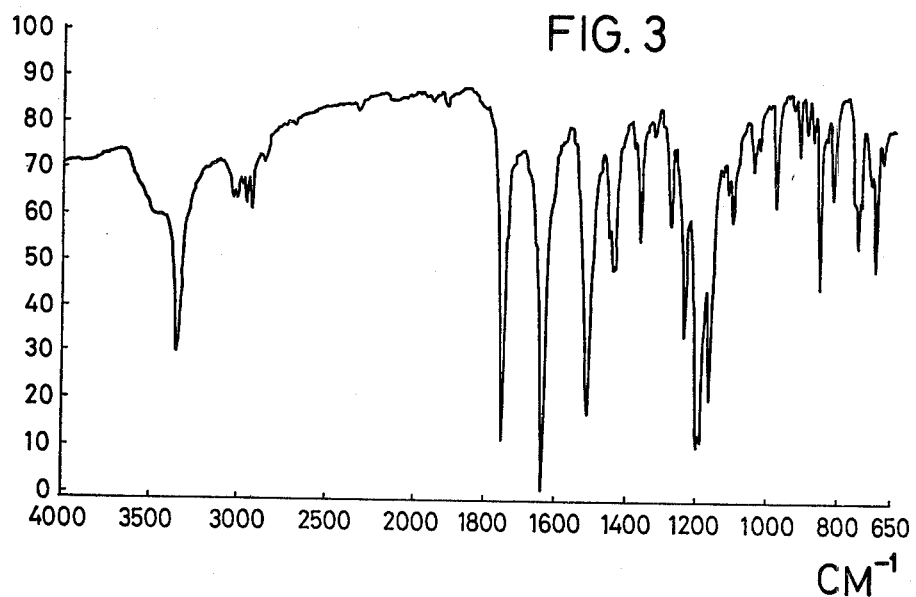

FIG. 3: N-(4-methylbenzylthiocarbonyl)-L-phenylalanine methylester (Compound No. 2)

Figure 4:
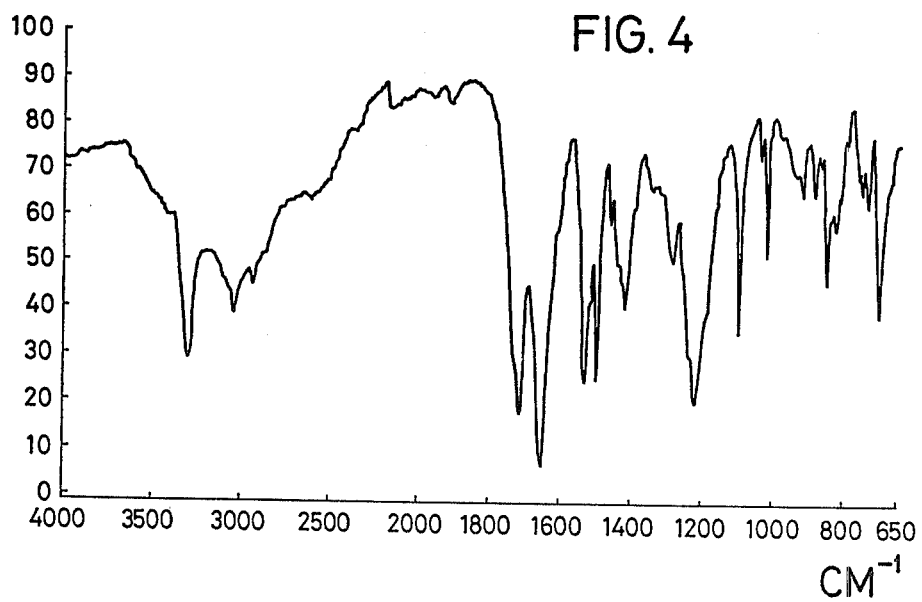

FIG. 4: N-(4-chlorobenzylthiocarbonyl)-L-phenylalanine (Compound No. 7)

Figure 5:
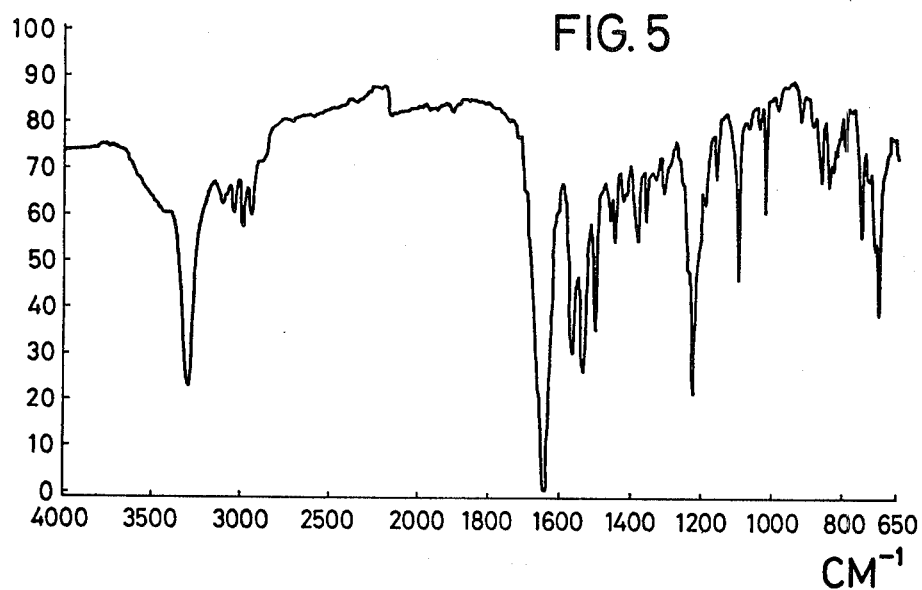

FIG. 5: N-(4-chlorobenzylthiocarbonyl)-L-phenylalanine ethylamide (Compound No. 10)

Figure 6:
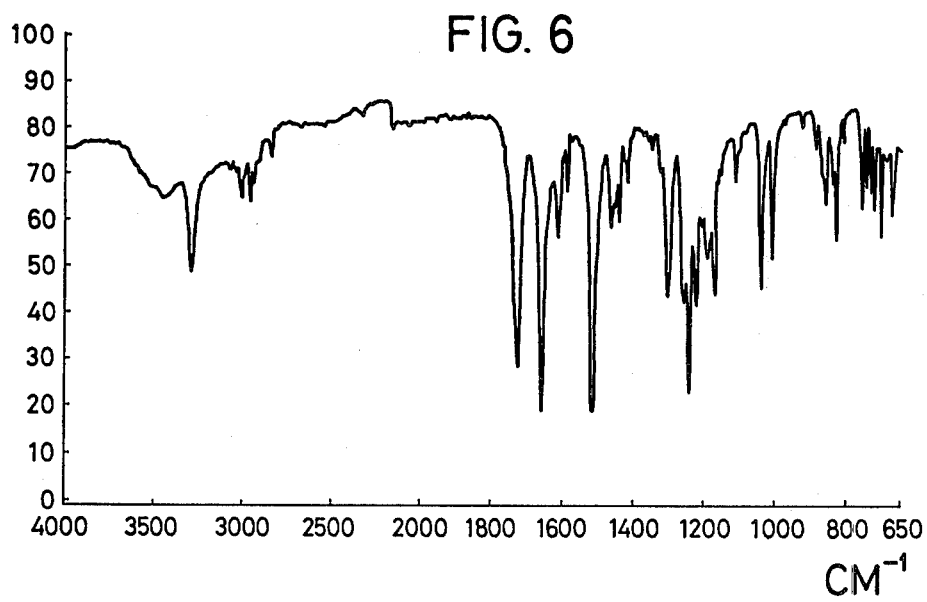

FIG. 6: N-(4-methoxybenzylthiocarbonyl)-L-phenylalanine methylester (Compound No. 13)

Figure 7:
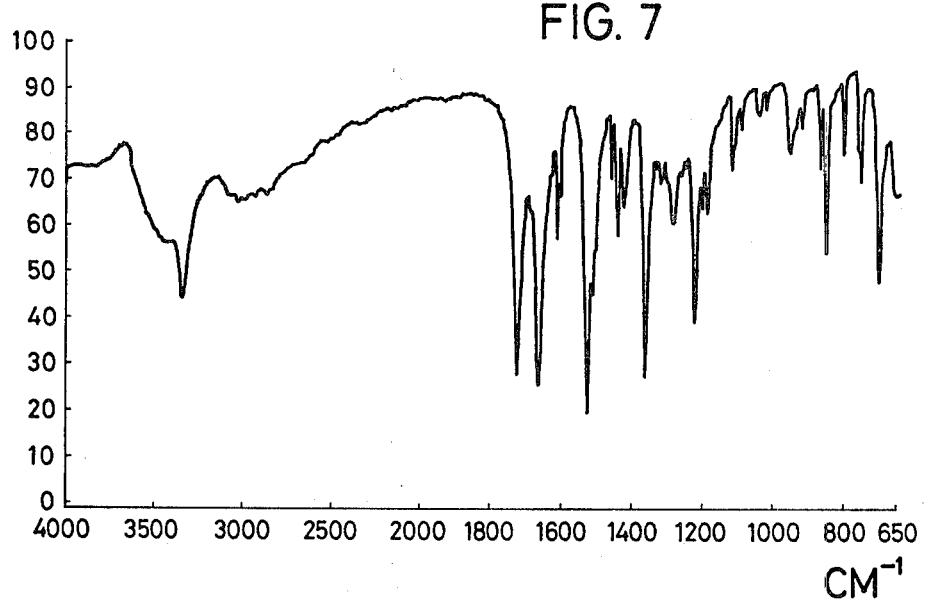

FIG. 7: N-(4-nitrobenzylthiocarbonyl)-L-phenylalanine (Compound No. 14)

Figure 8:
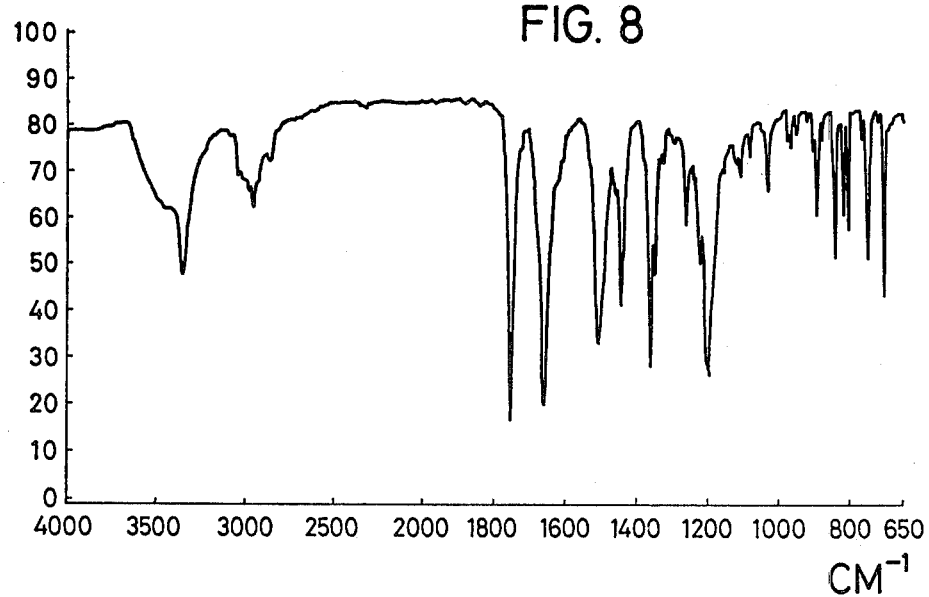

FIG. 8: N-(2,5-dimethylbenzylthiocarbonyl)-L-phenylalanine methylester (Compound No. 27)

Figure 9:
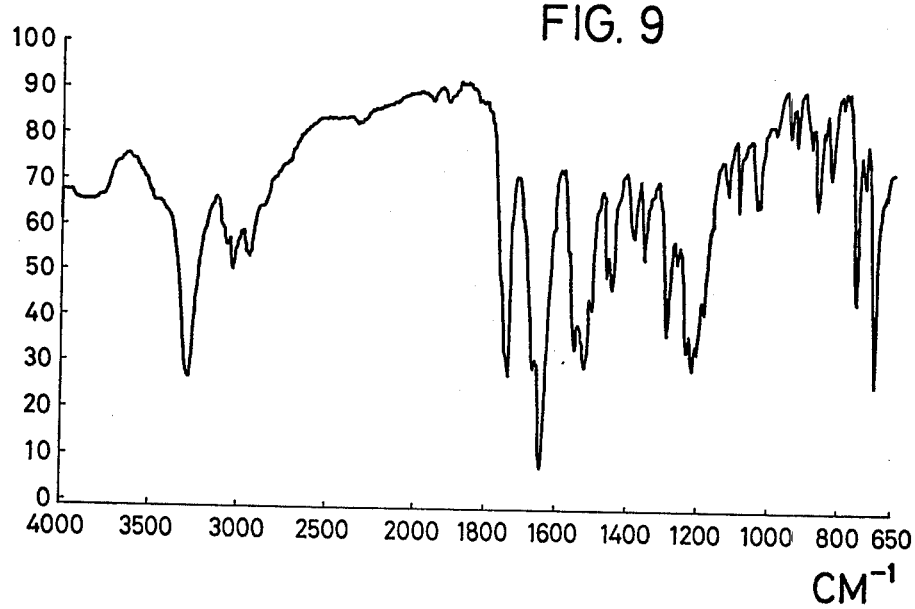

FIG. 9: N-(4-methylbenzylthiocarbonyl)-L-phenylalanyl-L-phenylalanine methylester (Compound No. 6)

Figure 10:
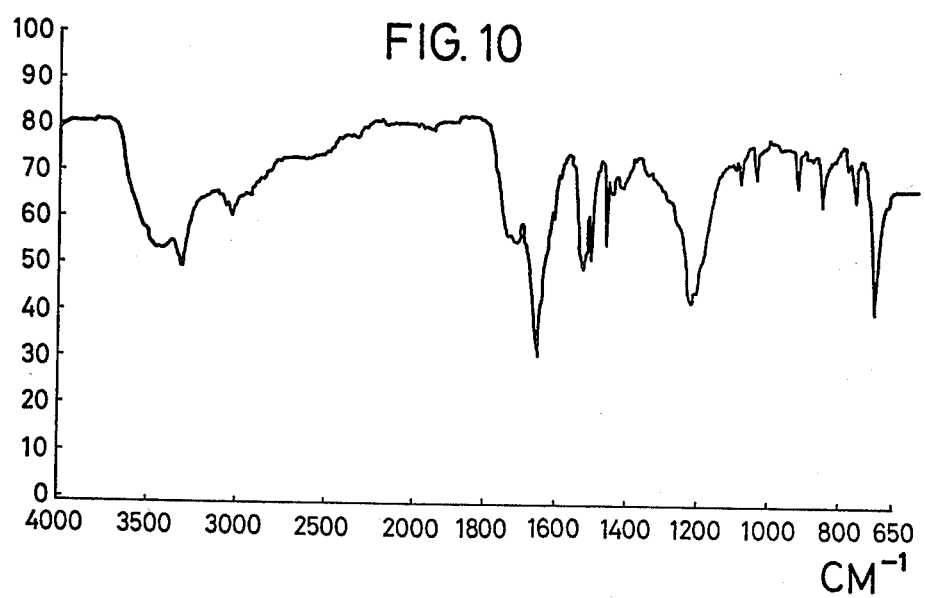

FIG. 10: N-benzylthiocarbonyl-L-phenylalanine (Compound No. 17)

NMR Spectrum —

Figure 11:
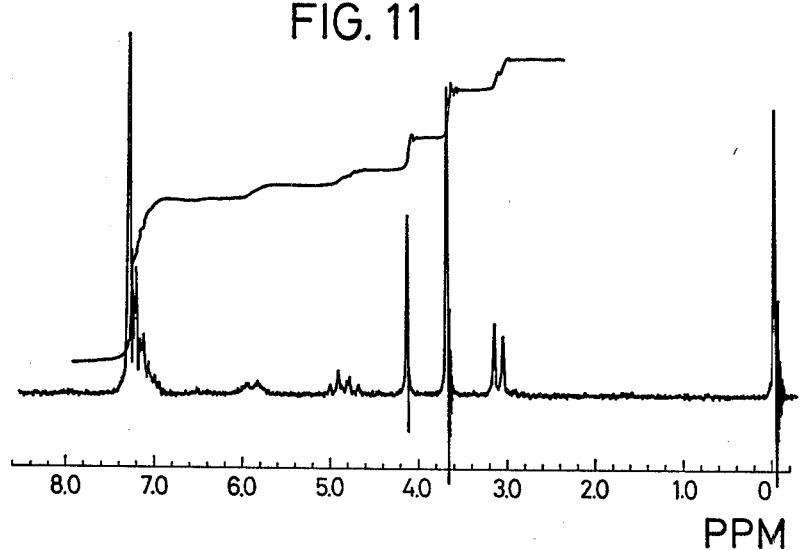

FIG. 11: N-benzylthiocarbonyl-L-phenylalanine methylester (Compound No. 18)

Figure 12:
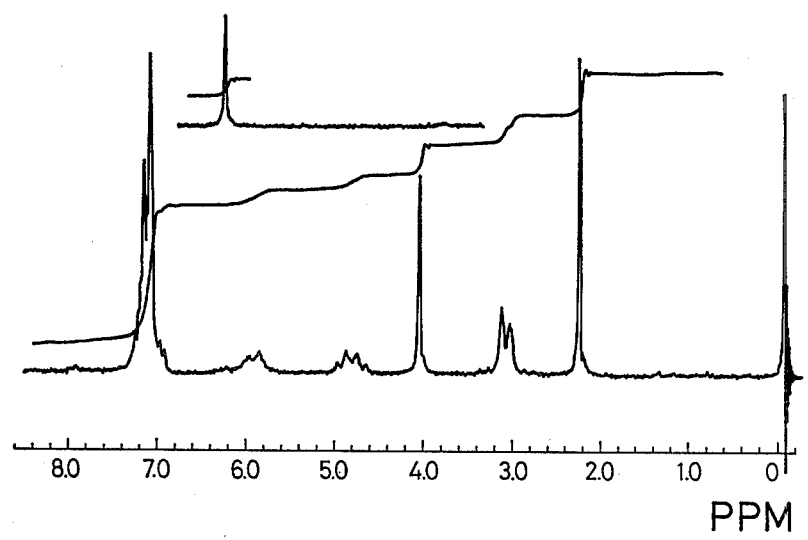

FIG. 12: N-(4-methylbenzylthiocarbonyl)-L-phenylalanine (Compound No. 1)

Figure 13:
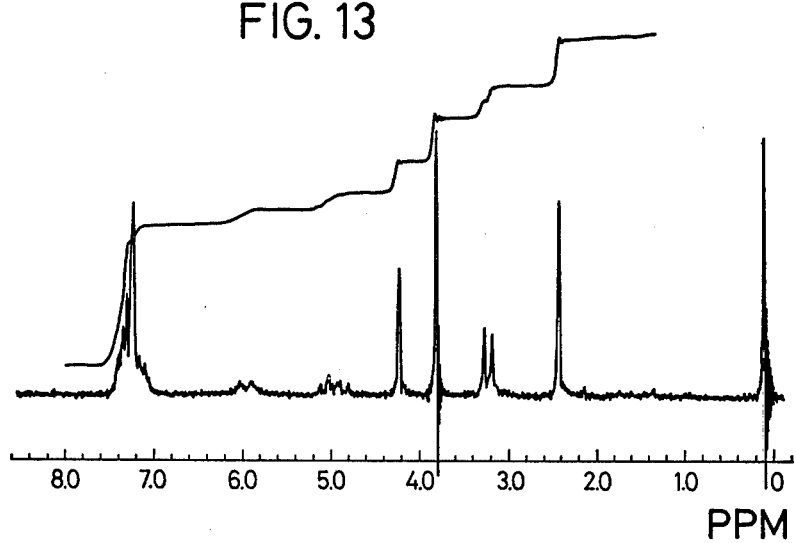

FIG. 13: N-(4-methylbenzylthiocarbonyl)-L-phenylalanine methylester (Compound No. 2)

Figure 14:
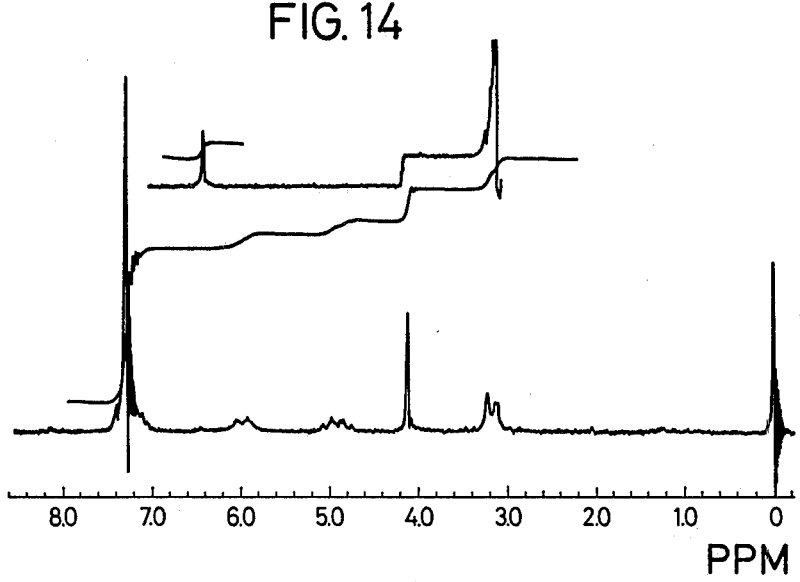

FIG. 14: N-(4-chlorobenzylthiocarbonyl)-L-phenylalanine (Compound No. 7)

Figure 15:
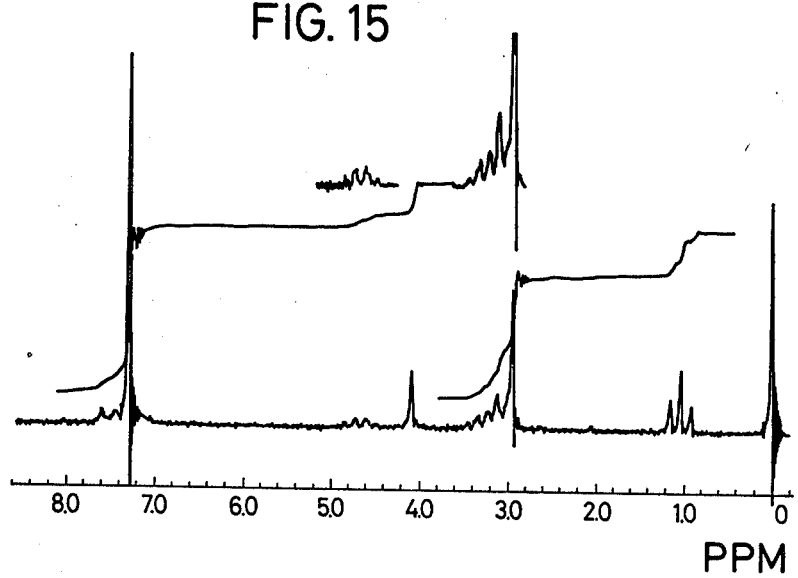

FIG. 15: N-(4-chlorobenzylthiocarbonyl)-L-phenylalanine ethylamide (Compound No. 10)

Figure 16:
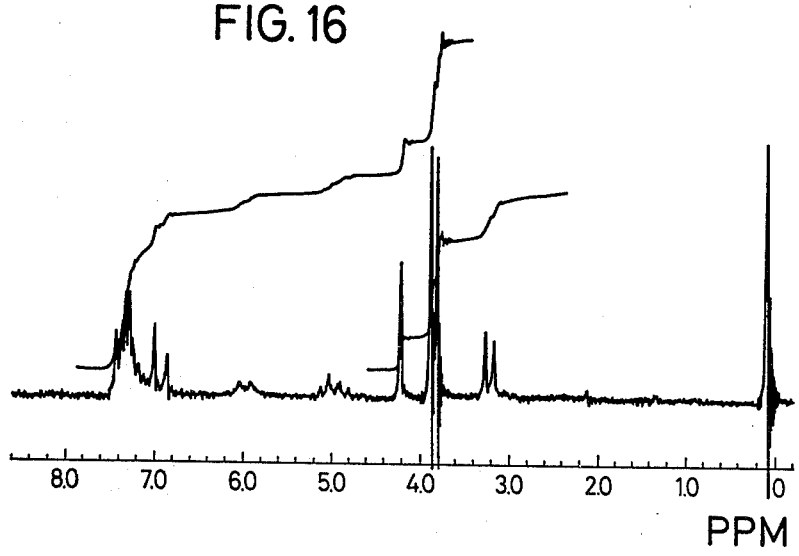

FIG. 16: N-(4-methoxybenzylthiocarbonyl)-L-phenylalanine methylester (Compound No. 13)

Figure 17:
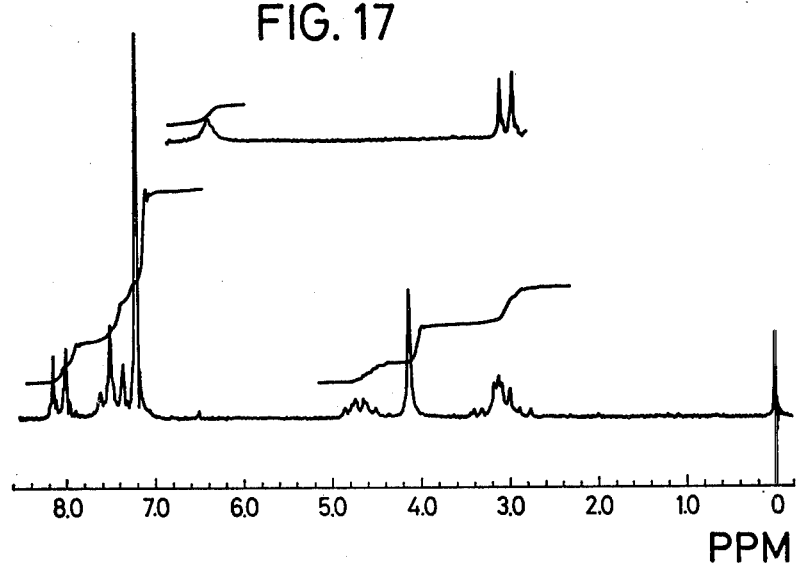

FIG. 17: N-(4-nitrobenzylthiocarbonyl)-L-phenylalanine (Compound No. 14)

Figure 18:
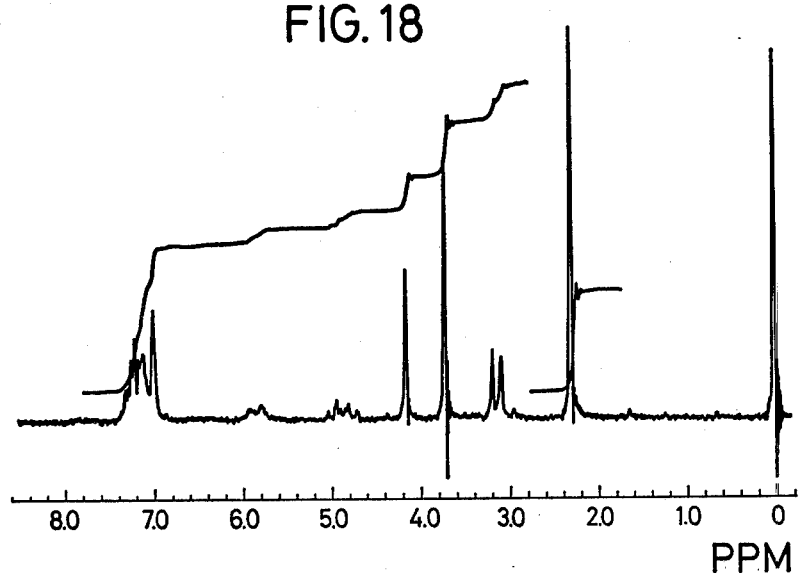

FIG. 18: N-(2,5-dimethylbenzylthiocarbonyl)-L-phenylalanine methylester (Compound No. 27)

Figure 19:
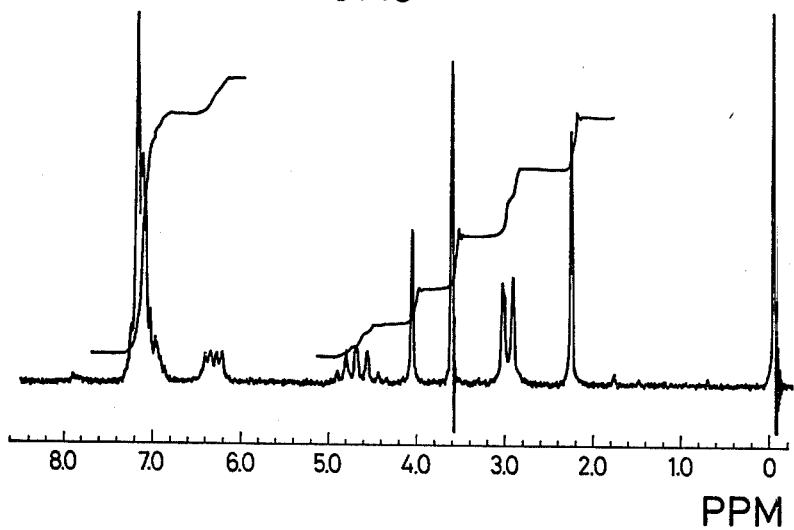

FIG. 19: N-(4-methylbenzylthiocarbonyl)-L-phenylalanyl-L-phenylalanine methylester (Compound No. 6)

Figure 20:
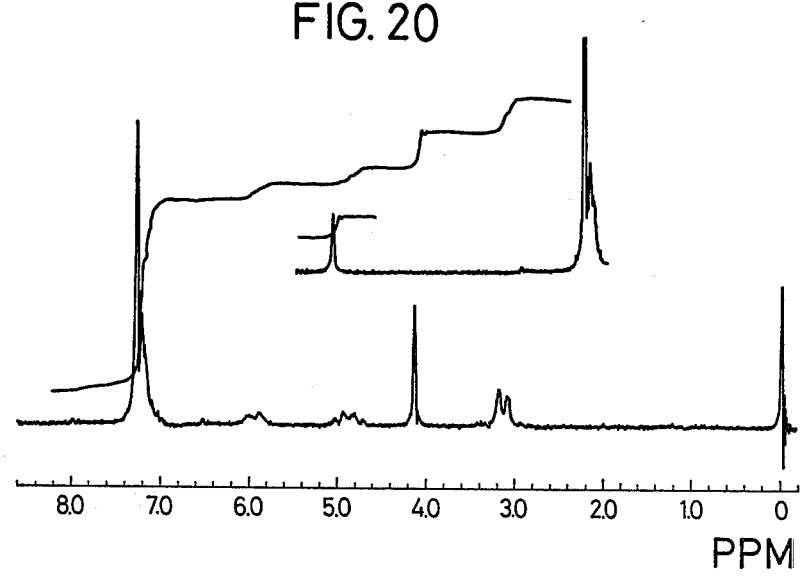

FIG. 20: N-benzylthiocarbonyl-L-phenylalanine (Compound No. 17)

Note: NMR spectrum — The internal standard was trimethylsilane. As the solvent, CDCl$_3$ was used. In FIGS. 15 and 16, a mixture of CDCl$_3$ and N,N-dimethylformamide (Volume ratio - 2:1) was used.

The pharmacological activities of the derivatives of phenylalanine of formula (I) are as follows.

(1) Acute toxicity and tonic convulsion in hind paw:

The acute toxicity and tonic convulsion occured by stimulus by hand touch were determined in the following manner to give the results shown in Table 2.

(a) Acute toxicity in mice:

38 Groups, each consisting of 5 mice (male dd-strain, weight — 18 to 24 g), were used for the test and control groups. The compounds shown in Table 2 were administered orally or intraperitoneally to the mice. After one week, the survival ratio was measured.

(b) Acute toxicity in rats:

28 Groups, each consisting of 5 rats (male Wistar strain, weight — 200 g), were used for the test and control groups. The compounds shown in Table 2 were orally administered to the rats. After one week, the survival ratio was measured.

(c) Tonic convulsion of hind paw of mice:

38 Groups, each consisting of 5 mice (male dd-strain, weight — 18 to 24 g), were used for the test and control groups. The compounds shown in Table 2 were orally administered to the mice. At 30, 60, 120, 180 and 360 minutes after the administration, stimulus by hand touch was given to the mice and the tonic convulsion was observed. When at least one convulsion of hind paw was observed at any time, this occurence was marked with "positive".

the acute toxicity of the derivatives of phenylalanine of formula (I) was relatively weak. Namely, the tonic convulsion of hind paw was observed when Clofibrate (500 mg/kg) was orally administered while not observed by the administration of almost all of N-benzyl-thiocarbonyl-L-phenylalanine or its derivatives.

Table 2

| Test Compound | Acute Toxicity (LD$_{50}$) | | | Tonic convulsion | |
|---|---|---|---|---|---|
| | Mouse | | Rat | | Tonic |
| | A mg/kg | B mg/kg | C mg/kg | D | convulsion |
| Clofibrate | 2100 | 1625 | >200 | 500 | + |
| Compound 1 | >4000 | >100 | >200 | 4000 | − |
| " 2 | >4000 | >100 | >900 | 4000 | − |
| " 3 | >1000 | | | 1000 | − |
| " 4 | >1000 | >100 | >100 | 1000 | − |
| " 5 | >1000 | >100 | >100 | 1000 | − |
| " 6 | >300 | >100 | >100 | | |
| " 7 | >300 | >100 | >100 | 300 | − |
| " 8 | >4000 | >100 | >200 | 4000 | − |
| " 9 | >1000 | >100 | >100 | 1000 | − |
| " 10 | >300 | >100 | >100 | 300 | − |
| " 11 | >300 | >100 | >100 | 300 | − |
| " 12 | >1000 | | >100 | 1000 | + |
| " 13 | >1000 | >100 | >100 | 1000 | − |
| " 14 | >1000 | | >100 | 1000 | − |
| " 15 | >1000 | | >100 | 1000 | − |
| " 16 | >1000 | | >200 | 500 | + |
| " 17 | >1000 | | >100 | 1000 | + |
| " 18 | >1000 | | >200 | 500 | + |
| " 19 | >1000 | | >100 | 1000 | − |
| " 20 | >1000 | | | 1000 | + |
| " 21 | >1000 | | | 1000 | + |
| " 22 | >1000 | | | 1000 | + |
| " 23 | >1000 | | | 1000 | − |
| " 24 | >1000 | | >100 | 1000 | − |
| " 25 | >1000 | | >100 | 1000 | − |
| " 26 | >1000 | | >100 | 1000 | − |
| " 27 | >1000 | | >100 | 1000 | − |
| " 28 | >1000 | | >100 | | |
| " 29 | >1000 | | >100 | 1000 | − |
| " 30 | >1000 | | >100 | 1000 | − |
| " 31 | >1000 | | >100 | 1000 | − |
| " 32 | >1000 | | >100 | 1000 | − |
| " 33 | >1000 | | | 1000 | − |
| " 34 | >1000 | | | 1000 | − |
| " 35 | >1000 | | | 1000 | − |
| " 36 | >1000 | | | 1000 | − |
| " 37 | >1000 | | | 300 | − |

Note:
A - Oral administration
B - Intraperitoneal administration
C - Oral administration
D - Amount of administration (oral)

(2) Cholesterol-Lowering activity on hyperlipemia induced by Triton in mice:

The cholesterol-lowering activity was confirmed by the activity on hyperlipemia induced by Triton in the following manner and the results are shown in Table 3.

38 Groups, each consisting of 9 mice (male dd-strain, weight — 19 to 21 g), were used for the test and control groups. Each mouse was intravenously administered with 600 mg/kg of Triton (WR-1339). Immediately after the administration and also after 20 hours from the administration of Triton, the mice were orally administered with 100 mg/kg of the compound shown in Table 3. 43 hours after the administration of Triton, the blood samples were collected by decapitation and then the corpuscle was removed by centrifugation. Cholesterol in the serum was determined by Zurkowski's method modified by Shibata (color of the test solution was developed by using sulfoalicyclic acid, acetic acid and sulfuric acid and the optical density of the solution was determined at 620 m$\mu$.

Table 3

| Compound No. | Ratio of the reduction of cholesterol (%) | Compound No. | Ratio of the reduction of cholesterol (%) |
|---|---|---|---|
| 1 | 55 | 20 | 47 |
| 2 | 38 | 21 | 43 |
| 3 | 57 | 22 | 46 |
| 4 | 23 | 23 | 48 |
| 5 | 0 | 24 | 34 |
| 6 | 39 | 25 | 37 |
| 7 | 94 | 26 | 43 |
| 8 | 88 | 27 | 30 |
| 9 | 57 | 28 | 50 |
| 10 | 43 | 29 | 59 |
| 11 | 75 | 30 | 68 |
| 12 | 76 | 31 | 74 |
| 13 | 56 | 32 | 56 |
| 14 | 66 | 33 | 79 |
| 15 | 29 | 34 | 11 |
| 16 | 86 | 35 | 22 |
| 17 | 95 | 36 | 83 |
| 18 | 80 | 37 | 74 |
| 19 | 84 | Clofibrate | 40 |

(3) Cholesterol-lowering activity on normal rats of Wistar strain:

(i) 22 Groups, each consisting of 5 rats (male Wistar strain, weight — 150 to 180 g) were used for the test and control groups. The rats were fed with powdery diet containing 0.3% (by weight) of the compounds shown in Table 4 for 4 or 14 days. After this, the blood samples were collected by decapitation and then the corpuscle was removed by centrifugation. Cholesterol in the serum was determined by Zurkowski's method modified by Shibata and also the liver was excised and weighed. The results are shown in Table 4 wherein the ratio of 100% denotes the amount of chloresterol and the weight of the liver of normal rats fed with powdery diet without the addition of the compound.

Table 4

| Compound | Continuous administration for 4 days | | Continuous administration for 14 days | |
|---|---|---|---|---|
| | A(%) | B(%) | C(%) | D(%) |
| Clofibrate | 58.4 | 40.1 | 32.3 | 60.1 |
| Compound 1 | 44.6 | 14.8 | 26.1 | 33.1 |
| " 2 | 18.0 | 8.2 | 17.5 | 3.9 |
| " 4 | 30.5 | 6.2 | | |
| " 8 | 4.7 | 138 | | |
| " 9 | 33 | 71 | | |
| " 12 | 28.1 | 45.9 | | |
| " 13 | 21.9 | 38 | | |
| " 14 | 44.3 | 48.0 | | |
| " 15 | 40.4 | 38.9 | | |
| " 16 | | | 9.2 | 79 |
| " 17 | 42.7 | 35.2 | | |
| " 18 | 43.8 | 39 | 3.0 | 92 |
| " 19 | 34.8 | 19.8 | | |
| " 24 | 28.4 | 15.0 | | |
| " 25 | 25.1 | 45.3 | | |
| " 26 | 21.3 | 0.8 | | |
| " 27 | 14.5 | −0.2 | | |
| " 28 | 26.7 | 10.6 | | |
| " 30 | 4.5 | 11.0 | | |
| " 31. | 14.9 | 24.4 | | |
| " 32 | 24.2 | 12.4 | | |

Note:
A - Ratio of decrease of cholesterol
B - Ratio of decrease of liver weight
C - Ratio of decrease of cholesterol
D - Ratio of increase of liver weight (ii) Determination of triglyceride, phospholipid and free fatty acid in the serum of normal rats of Wistar strain:

Clofibrate and Compounds 1 and 2 were tested in a similar manner to that described in (i). Triglyceride, phospholipid and free fatty acid in the serum were determined in the following manner to give the results shown in Table 5.

(a) Determination of triglyceride:

Triglyceride was determined by acetylacetone method [Kazuo Matsumiya et al "Rinsho Byori", Vol. 18, page 383 (1970), Japan] in the following manner.

Isopropyl alcohol was added to the test solution of the serum to extract triglyceride which was then saponified with potassium hydroxide to give glycerol. The glycerol was oxidized by using sodium salt of methaperiodic acid to convert it into formaldehyde. Color of the test solution was developed by acetylacetone and the optical density at 420 m$\mu$ was determined.

(b) Determination of phospholipid:

"Phospholipid Test Wako", a reagent available from Wako Junyaku K.K., Japan, was used for the determination of phospholipid in the following manner according to a similar manner to that described in "Rinsho Byori", Vol. 17, page 389 (1969), Japan, by Atsuo Ichida et al.

Trichloroacetic acid was added to the serum to give precipitates of lipoprotein which were then added with sulfuric acid and potassium permanganate to form phosphoric acid. Color of the test solution was developed by ammonium molybdate and the optical density was determined at 660 m$\mu$.

(c) Determination of free fatty acid:

Laurell's method [CLin. Chim. Acta. 16, 57 (1967)] was used for determination in the following manner.

250 mg of silicic acid and 6 ml of an extracting solution (chloroform : heptane = 4:3) containing 2% methanol were put into a centrifugation tube and added with 0.05 ml of the serum. After shaking for 5 minutes, the solution was centrifuged. 5 Ml of the supernatant was put into another tube and was added with 2 ml of copper reagent. The solution was shaken well for 5 minutes and centrifuged. 3 Ml of the supernatant was added with 0.5 ml of 0.4% diphenylcarbazide to develope color. The optical density at 550 m$\mu$ was determined. The results are shown in Table 5, from which it is apparent that Compounds 1 and 2 have a lowering activity on lipids other than cholesterol.

Table 5

| Compound | Continuous administration for 4 days | | |
|---|---|---|---|
| | A(%) | B(%) | C(%) |
| Clofibrate | 50.1 | 25.0 | 26.7 |
| Compound 1 | 42.0 | 13.8 | 27.0 |
| Compound 2 | 2.1 | 10.9 | 21.8 |

Note:
A - Ratio of decrease of triglyceride
B - Ratio of decrease of phospholipid
C - Ratio of decrease of free fatty acid (4) Effect on hyperlipemia induced by Triton in rats:

(i) Activity in the increasing phase:

3 Groups, each consisting of 9 rats (male Wistar strain, weight — 200 to 240 g) fasted for 24 hours were used for this test. Each rat was administered intravenously with 200 mg/kg of Triton (WR-1339), followed by oral administration of 200 mg/kg of the compounds shown in Table 6. After 20 hours from the administration, the blood samples were collected by decapitation. Cholesterol and triglyceride in the serum were determined in a similar manner to that used in (2, ii) to give the results shown in Table 6.

Table 6

| | Cholesterol | | Triglyceride | |
|---|---|---|---|---|
| Compound | (mg/ml) | Ratio of decrease(%) | (mg/ml) | Ratio of decrease(%) |
| Control | 255.5 | — | 1337 | — |
| Clofibrate | 203.4 | 20.8 | 856 | 36.0 |
| Compound 1 | 198.5 | 22.7 | 940 | 29.7 |
| Compound 2 | 202.0 | 21.3 | 729 | 45.5 |

(II) Activity in the decreasing phase:

Hyperlipemia occurred by administering Triton (WR-1339) in a similar manner to that in (i). After 25 hours, 200 mg/kg of the compounds were orally administered to the rats. After 30 hours from the injection of Triton, the blood samples were collected by decapitation. Cholesterol and triglyceride in the serum were determined to give the results shown in Table 7, from which it is apparent that the activities of Clofibrate, Compounds 1 and 2 are substantially equal in the developing phase while the activities of Compounds 1 and 2 are superior to that of Clofibrate in the decreasing phase.

Table 7

| | Cholesterol | | Triglyceride | |
|---|---|---|---|---|
| Compound | (mg/ml) | Ratio of decrease(%) | (mg/ml) | Ratio of decrease(%) |
| Control | 148.7 | — | 347.2 | — |
| Clofibrate | 137.6 | 7.5 | 401.2 | −15.6 |
| Compound 1 | 103.1 | 30.7 | 141.2 | 59.4 |
| Compound 2 | 115.8 | 22.2 | 205.4 | 40.9 |

(5) Lipid lowering effects on glycerol induced hyperlipemia in rats:

The test was carried out in a similar method to that by Nikkila et al [Life Science, 3, 1021 (1964)].

A group consisting of 10 rats (male Wistar strain, weight - 190 to 210 g) was used for each of the test and control groups. Hyperlipemia occurred by feeding the rats ad libitum with water containing 15% (by volume) of glycerol. Meanwhile a powdery diet containing 0.25% (by weight) of the compound was fed ad libitum. After this, the blood samples were collected by decapitation and the serum was separated by centrifugation. Cholesterol and triglyceride in the serum were determined to give the results shown in Table 8, from which it is apparent that Clofibrate, Comounds 1 and 2 have an activity on lowering triglyceride and cholesterol.

Table 8

| | Cholesterol | | Triglyceride | |
|---|---|---|---|---|
| Compound | (mg/ml) | Ratio of decrease(%) | (mg/ml) | Ratio of decrease(%) |
| Normal rat | 48.4 | — | 59.7 | — |
| Control | 56.3 | — | 494.2 | — |
| Clofibrate (0.25%) | 39.1 | 30.6 | 128.6 | 74.0 |
| Compound 1 (0.25%) | 44.5 | 21.0 | 148.4 | 70.0 |
| Compound 2 (0.25%) | 47.5 | 15.7 | 260.7 | 41.3 |

(6) Lipid lowering activity in cynomolgus monkeys:

6 cynomolgus monkeys (male, born in Malaysia, weight — 2.5 to 3.9 kg) were used for this test. All monkies were breeded in individual cages at a temperature from 23° to 25° C. and fed with a solid diet for monkey (available from Oriental Yeast K.K., Japan) and sweet potatoes every morning and with apples and bananas from time to time. The monkeys were divided into 3 groups, each consisting of 2 monkeys, to orally and compulsively administer the test compound in an amount of 100 mg/kg/day once in every morning for 10 days. At 11 days after the first administration, before feeding the diet in early morning blood samples were collected from the saphenae of the monkeys to determine cholesterol and triglyceride in a similar manner to that described above. The ratio of lowering cholesterol (RCL) or triglyceride (RLT) was calculated by the following formula.

$$RLC \text{ or } RLT = \frac{(A - B)}{A} \times 100\%$$

wherein A is the average amount of the cholesterol or triglyceride in the serum before administration, and B is the corresponding amont after administration for 10 days.

After an interval of 5 weeks, another compound was administered to determine cholesterol or triglyceride in a similar manner to that described above. After a further interval of 5 weeks, a similar procedure was repeated by using another compound to determine cholesterol or triglyceride. The values obtained by 3 times cross-over of the tests were averaged to give the results shown in Table 9, which indicates that Clofibrate, Compounds 1 and 2 have a cholesterol-lowering activity.

Table 9

| Compound* | Decrease Ratio of Cholesterol (%) | Decrease Ratio of Triglyceride (%) |
|---|---|---|
| Clofibrate | 6.7 | 9.0 |
| Compound 1 | 12.2 | 10.8 |
| Compound 2 | 9.7 | −7.3 |

Note: *100 mg/kg × 10

As apparent from the above-mentioned results, the derivatives of phenylalanine of formula (I) have an excellent lipid-lowering activity and a low toxicity.

These compounds can be administered orally to human and the dosage may preferably be from 0.5 to 3.0 g per day for adult (weight: 50 to 60 Kg). For oral administration, the compounds of formula (I) may be preferably in the forms of a tablet, capsule or powder, and if desired, excipients (e.g. lactose, glucose, manitol and the like), disintegrators (e.g. potato starch, carboxymethyl cellulose, sodium arginate and the like), lubricants (e.g. magnesium stearate, talc and the like) and binders (e.g. polyvinylalcohol, polyvinylpyrrolidone and the like) may be associated therewith.

The following non-limitative examples illustrate the invention.

EXAMPLE 1

Preparation of N-benzylthiocarbonyl-L-phenylalanine:

9.9 G (0.06 mol) of L-phenylalanine and 5.8 g (0.055 mol) of sodium carbonate were dissolved in 150 ml of water, into which 3.0 g (0.05 mol) of carbonyl sulfide was blown at a temperature of from 10° to 15° C. in 30 minutes. The mixture was then stirred for 30 minutes. To the mixture was added 6.3 g (0.05 mol) of benzylchloride dissolved in 90 ml of acetone dropwise in 15 minutes and the mixture was stirred for 2 hours at room temperature. After completion of the reaction, acetone was removed off from the solution by evaporating under reduced pressure. The residue was washed with 100 ml of benzene and the aqueous layer was acidified with concentrated hydrochloric acid to liberate an oily substance which was extracted twice with ethylacetate (each 100 ml). The ethylacetate layer was washed twice with water (each 100 ml) and was dried over anhydrous sodium sulfate. After drying, the drying agent was filtered. The filtrate was evaporated under reduced pressure to give a syrup-like substance which were added with 20 ml of ether and 50 ml of n-hexane. The mixed solution was stood in cold place to obtain 11.6 g of white powdery substance.

Melting point: 63°–65° C.
Yield : 73.7%

| Elementary analysis as $C_{17}H_{17}NO_3S$: | | |
|---|---|---|
| C(%) | H(%) | N(%) |
| Found 64.82 | 5.32 | 4.71 |
| Calculated 64.74 | 5.43 | 4.44 |

EXAMPLE 2

Preparation of N-benzylthiocarbonyl-L-phenylalanine methylester:

10.8 G (0.05 mol) of L-phenylalanine methylester hydrochloride was suspended in 100 ml of chloroform, to which was added 13.9 ml (0.1 mol) of triethylamine while cooling with ice. Into the solution was blown 3.0 g (0.05 mol) of carbonyl sulfide at a temperature of from 5° to 10° C. in 15 minutes. The mixture was stirred for 15 minutes at the same temperature as above and was then added dropwise with 20 ml of chloroform solution containing 6.3 g (0.05 mol) of benzylchloride at a temperature of from 10° to 15° C. in 10 minutes. The mixture was then stirred for 3 hours at room temperature. After completion of the reaction, the reaction solution was washed twice with water (each 100 ml), 100 ml of 2N hydrochloric acid and 150 ml of water in subsequence and was dried over anhydrous sodium sulfate. After drying, the drying agent was filtered. The filtrate was evaporated in vacuo to give a syrup-like substance which was added with 30 ml of ethylacetate and 50 ml of n-hexane. Thus, in a similar manner to that described in Example 1, 11.2 g of white crystals were obtained.

Melting point: 46°–47° C.
Yield : 68.1% -methylbenzylthiocarbonyl)-L-phenylalanine

| Elementary analysis as $C_{18}H_{19}NO_3S$: | | |
|---|---|---|
| C(%) | H(%) | N(%) |
| Found 65.87 | 5.89 | 4.30 |
| Calculated 65.63 | 5.81 | 4.25 |

EXAMPLE 3

Preparation of N-(4-methylbenzylthiocarbonyl)-L-phenylalanine:

16.5 G (0.1 mol) of L-phenylalanine and 27.8 ml (0.2 mol) of triethylamine were dissolved in 100 ml of water. To this solution was added dropwise 150 ml of dioxane containing 6.0 g (0.1 mol) of carbonyl sulfide at a temperature of from 5° to 10° C. in 15 minutes while cooling with ice. After stirring at a temperature of 10° C. for 15 minutes, 14.1 g (0.1 mol) of 4-methylbenzylchloride was added dropwise to the solution in 10 minutes and the solution was then stirred at room temperature for 1 hour. After completion of the reaction, a syrup-like substance was formed in a similar manner to that described in Example 1, which was then crystallized from 60 ml of ethylacetate and 300 ml of petroleum ether to obtain 25.7 g of white crystals.
Melting point: 92°–93° C.
Yield: 78.1%

| Elementary analysis as $C_{18}H_{19}NO_3S$: | | | |
|---|---|---|---|
| | C(%) | H(%) | N(%) |
| Found | 65.71 | 5.82 | 4.20 |
| Calculated | 65.63 | 5.81 | 4.25 |

EXAMPLE 4

Preparation of N-(4-chlorobenzylthiocarbonyl)-L-phenylalanine ethylamide 3.4 G (0.015 mol) of L-phenylalanine ethylamide hydrochloride was added to 80 ml of chloroform. To the mixture was added 3.3 ml (0.03 mol) of N-methyl-morphorine while cooling with ice. To the solution was dropwise added 20 ml of chloroform solution containing 0.9 g (0.015 mol) of carbonyl sulfide at a temperature of from 5° to 10° C. in 20 minutes. After stirred for 30 minutes at the same temperature, 30 ml of chloroform solution containing 2.4 g (0.015 mol) of 4-chlorobenzychloride was dropwise added to the solution in 30 minutes. After this, the solution was stirred at room temperature for 1 hour. The solid material obtained in a similar manner to that described in Example 2 was recrystallized from 50 ml of ethylacetate and 50 ml of n-hexane to give 4.1 g of white crystals.
Melting point: 158.5°–159.5° C.
Yield: 72.6%

| Elementary analysis as $C_{19}H_{21}N_2O_2SCl$: | | | |
|---|---|---|---|
| | C(%) | H(%) | N(%) |
| Found | 60.44 | 5.59 | 7.53 |
| Calculated | 60.54 | 5.62 | 7.43 |

EXAMPLE 5

Preparation of N-(4-nitrobenzylthiocarbonyl)-L-phenylalanine 8.3 G (0.05 mol) of L-phenylalanine and 13.9 ml (0.1 mol) of triethylamine were dissolved in 50 ml of water. To the solution was added 100 ml of dioxane solution containing 8.6 g (0.5 mol) of 4-nitrobenzylchloride. 3.0 g (0.05 mol) of carbonyl sulfide was blown into the solution at a temperature of from 10° to 15° C. in 15 minutes. After completion of blowing, the mixture was subjected to reaction at room temperature for 2 hours. After completion of reaction, the solid material obtained in a similar manner to that described in Example 1 was recrystallized from 50 ml of ethylacetate and 20 ml of n-hexane to yield 9.4 g of pale yellow crystals.
Melting point: 149°–150° C.
Yield: 52.2%

| Elementary analysis as $C_{17}H_{16}N_2O_5S$: | | | |
|---|---|---|---|
| | C(%) | H(%) | N(%) |
| Found | 56.65 | 4.30 | 7.56 |
| Calculated | 56.65 | 4.48 | 7.77 |

EXAMPLE 6

Preparation of N-(2,5-dimethylbenzylthiocarbonyl)-L-phenylalanine methylester 10.8 G (0.05 mol) of L-phenylalanine methylester hydrochloride was added to 100 ml of chloroform. To the mixture was added 13.9 ml (0.1 mol) of triethylamine while cooling with ice. 20 Ml of a chloroform solution containing 3.0 g (0.05 mol) of carbonyl sulfide was dropwise added to the solution at a temperature of from 5° to 10° C. in 20 minutes. After stirring at the same temperature for 30 minutes, 30 ml of chloroform solution containing 7.7 g (0.05 mol) of 2.5-dimethylbenzylchloride was dropwise added to the solution in 30 minutes. After this, the mixture was stirred at room temperature for 1 hour. After completion of reaction, the reaction mixture was washed with 100 ml of water, 100 ml of 2N-hydrochloric acid and 150 ml of water in order twice and was dried over anhydrous sodium sulfate in a similar manner to that described in Example 2. After filtration of the drying agent, the syrup-like substance obtained by removing the solvent of the filtrate in vacuo was crystallized from 30 ml of ethylacetate and 50 ml of n-hexane to yield 10.8 g of white crystals.
Melting point: 63.5°–64° C.
Yield: 60.5%

| Elementary analysis as $C_{20}H_{23}NO_3S$: | | | |
|---|---|---|---|
| | C(%) | H(%) | N(%) |
| Found | 67.44 | 6.48 | 4.19 |
| Calculated | 67.20 | 6.49 | 3.92 |

EXAMPLE 7

Preparation of N-(α-naphthylmethylthiocarbonyl)-L-phenylalanine 8.3 G (0.05 mol) of L-phenylalanine and 13.9 ml (0.1 mol) of triethylamine were dissolved in 100 ml of water. To the solution was dropwise added 100 ml of dioxane containing 3.0 g (0.05 mol) of carbonyl sulfide at a temperature of from 5° to 10° C. in 15 minutes while cooling with ice. After stirring at a temperature of 10° C. for 15 minutes, 8.8 g (0.05 mol) of 1-(chloromethyl)-naphthalene was dropwise added to the mixture in 10 minutes and the mixture was then stirred at room temperature for 1 hour. After completion of reaction, the syrup-like substance obtained in a similar manner to that described in Example 6 was crystallized from 80 ml of ether and 100 ml of n-hexane to yield 14.8 g of white crystals.
Melting point: 130°–132° C.
Yield: 81.1%

| Elementary analysis as $C_{23}H_{19}NO_3S$: | | | |
|---|---|---|---|
| | C(%) | H(%) | N(%) |
| Found | 69.15 | 5.10 | 3.63 |
| Calculated | 69.02 | 5.24 | 3.83 |

EXAMPLE 8

Preparation of N-(4-methylbenzylthiocarbonyl)-L-phenylalanine methylester 12.9 G (0.06 mol) of L-phenylalanine methylester hydrochloride was suspended in 100 ml of chloroform. To the suspension was added 16.7 ml (0.12 mol) of triethylamine for about 5 minutes while cooling with ice. To the mixture was dropwise added 12.0 g (0.06 mol) of 4-methylbenzylcarbonylchloride at a temperature of from 0° to 10° C. for about 15 minutes while cooling with ice. The mixture was then stirred at room temperature for 30 minutes, washed in turn with 100 ml of water, 100 ml of 2N-hydrochloric acid and about 100 ml of water, and then dried over anhydrous sodium sulfate. After drying, the drying agent was filtered. After removing the solvent of the filtrate by evaporation in vacuo, the residue was allowed to stand and solidify. The solid material was recrystallized from about 25 ml of ethylacetate and about 150 ml of n-hexane to yield 16.3 g of white crystals.

Melting point: 84°–86° C.
Yield: 79.2%

Elementary analysis as $C_{19}H_{21}O_3NS$:

|  | C(%) | H(%) | N(%) |
|---|---|---|---|
| Found | 66.35 | 6.26 | 4.34 |
| Calculated | 66.44 | 6.16 | 4.08 |

EXAMPLE 9

Preparation of N-(4-chlorobenzylthiocarbonyl)-L-phenylalanine 5.0 G (0.014 mol) of N-(4-chlorobenzylthiocarbonyl)-L-phenylalanine methylester obtained in a similar manner to that described in Example 8 was added to a mixture of 50 ml of concentrated hydrochloric acid and 50 ml of glacial acetic acid and refluxed for 30 minutes. After adding about 300 ml of water to the mixture, the resultant crystals were separated by filtration. After washing with water, the crystals were recrystallized from 10 ml of ethylacetate and about 50 ml of n-hexane to give 4.0 g of white crystals.

Melting point: 101°–103° C.
Yield: 83.2%

Elementary analysis as $C_{17}H_{16}NO_3SCl$:

|  | C(%) | H(%) | N(%) |
|---|---|---|---|
| Found | 58.43 | 4.58 | 4.14 |
| Calculated | 58.36 | 4.61 | 4.00 |

EXAMPLE 10

Preparation of N-(4-methylbenzylthiocarbonyl)-L-phenylalanyl-L-phenylalanine methylester 4.0 G (0.01 mol) of L-phenylalanyl-L-phenylalanine methylester hydrobromide was dissolved in 50 ml of water. To the solution was added 10 ml of an ether solution containing 2.21 g (0.011 mol) of 4-methylbenzylthiocarbonylchloride and was further dropwise added an aqueous solution containing 2.28 g (0.022 mol) of triethylamine for 15 minutes. After this, the mixture was stirred for 30 minutes while cooling with ice and was further stirred at room temperature for 4 hours. After completion of reaction, the reaction mixture was extracted with about 50 ml of ethylacetate. The ethylacetate layer was washed with 2N hydrochloric acid and then with water and was dried over anhydrous sodium sulfate. After drying, the drying agent was filtered. After removing the solvent of filtrate by evaporation in vacuo, the resultant solid material was recrystallized from 25 ml of ethylacetate and about 40 ml of n-hexane to obtain 3.7 g of white crystals.

Melting point: 115°–117° C.
Yield: 75.5%

Elementary analysis as $C_{28}H_{30}N_2O_4S$:

|  | C(%) | H(%) | N(%) |
|---|---|---|---|
| Found | 68.64 | 6.20 | 5.61 |
| Calculated | 68.55 | 6.16 | 5.71 |

EXAMPLE 11

Preparation of N-(4-hydroxybenzylthiocarbonyl)-L-phenylalanine methylester

3 Ml of thionyl chloride was dropwise added to 100 ml of anhydrous methanol at a temperature below −10° C. To the mixture was added 6 g (0.016 mol) of N-(4-acetoxybenzylthiocarbonyl)-L-phenylalanine synthesized according to Example 3. After the mixture was stirred at room temperature overnight, the solvent was evaporated under reduced pressure to obtain crude crystal. Further, the crude crystal was recrystallized from 30 ml ethyl acetate and 100 ml of n-hexane to obtain 5.1 g of white purified crystal.

Melting point: 113.5°–114.5° C.
Yield: 92.7%

Elementary analysis as $C_{18}H_{19}NO_4S$:

|  | C(%) | H(%) | N(%) |
|---|---|---|---|
| Found | 62.30 | 5.45 | 4.09 |
| Calculated | 62.59 | 5.54 | 4.06 |

EXAMPLE 12

Preparation of sodium N-(4-methylbenzylthiocarbonyl)-L-phenylalaninate 3.6 G (0.011 mol) of N-(4-methylbenzylthiocarbonyl)-L-phenylalanine was dissolved in 10 ml of acetone. To the mixture were added 30 ml of water and 10 ml of 1N-sodium hydroxide and then the mixture was stirred at room temperature for 1 to 2 minutes to obtain a transparent solution. After the solution was washed with 30 ml of ether twice, the water layer was evaporated under reduced pressure. To remove the remaining amounts of water from the residue, a small quantity of ethanol was added to the residue and then evaporated under reduced pressure. This operation was repeated three times. Thus, the residue was completely dried to obtain 3.4 g of white powder of the desired sodium salt.

Melting point: 230° C. (decomp.)
Optical rotation: $[\alpha]_D^{26} = -12.7$ (C=1.0 in ethyl acetate)

EXAMPLE 13

The following compounds were synthesized in a similar manner to that described in Example 8.

N-(4-tert-butylbenzylthiocarbonyl)-L-phenylalanine methylester (In formula (I), A : $(CH_3)_3$—C—⟨phenyl⟩— and R : —$OCH_3$)

N-(4-methylbenzylthiocarbonyl)-L-phenylalanine diethylamide (In formula (I), A : $H_3C$—⟨phenyl⟩— and R : —$N(C_2H_5)_2$)

-continued

N-(4-methylbenzylthiocarbonyl)-L-phenylalanine morphoride (In formula (I), A : H₃C— 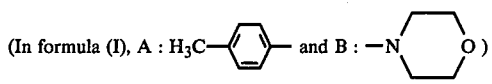 and B : —N⟨O⟩ )

N-(4-methoxybenzylthiocarbonyl)-L-phenylalanine diethylamide (In formula (I), A : H₃CO— 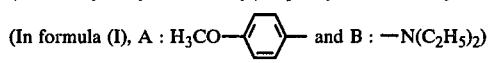 and B : —N(C₂H₅)₂)

N-(4-methoxybenzylthiocarbonyl)-L-phenylalanine morphoride (In formula (I), A : H₃CO— 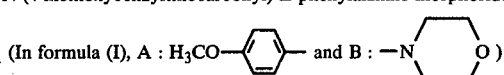 and B : —N⟨O⟩ )

N-(4-chlorobenzylthiocarbonyl)-L-phenylalanine diethylamide

[In general formula (I), A : Cl— 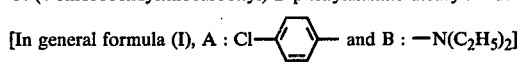 and B : —N(C₂H₅)₂]

N-(4-chlorobenzylthiocarbonyl)-L-phenylalanine morphoride (In general formula (I), A : Cl— 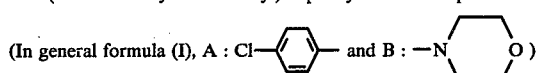 and B : —N⟨O⟩ )

All the compounds obtained were syrup-like. The melting point and elementary analysis thereof were not determined.

EXAMPLE 14

Tablet:

| Component (for 10,000 tablets): | |
|---|---|
| Compound 1 | 2500.0 (g) |
| Potato starch | 667.5 |
| Carboxymethylcellulose calcium | 175 |
| Polyvinyl alcohol | 122.5 |
| Magnesium stearate | 35.0 |

Compound 1, potato starch and carboxymethyl cellulose calcium in an amount stated above were blended in a twin-shell blender to produce well mixed powders. Granules were prepared by conventional wet granulation method using polyvinyl alcohol as a binder. The granules were mixed with magnesium stearate and formed into tablets using a flat face bevel edge punch having a diameter of 10 mm. Tablets, each having a diameter of 10 mm, a thickness of 4.0 mm and a weight of 350 mg, were prepared.

EXAMPLE 15

Capsule:

| Component (for 10,000 capsules) | |
|---|---|
| Compound 1 | 2500.0 (g) |
| Potato starch | 410.0 |
| Magnesium stearate | 90.0 |

The above components were well mixed in a twin-shell blender. The mixed powders were packed in No. 1 hard capsules. The contents in one capsule was 300 mg.

EXAMPLE 16

Powder

| Component: | | |
|---|---|---|
| Compound 2 | 200 | (g) |
| Lactose | 800 | |

The above components were well mixed in a twin-shell blender.

What is claimed is:

1. A compound of the formula and pharmaceutically acceptable salts thereof:

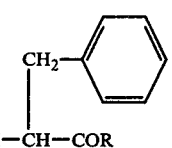

$$A-CH_2-SCONH-CH-COR$$

[I]

wherein A is selected from the group consisting of a naphthyl group, a substituted phenyl group having 1 to 5 substituents selected from the group consisting of a $C_1$ to $C_5$ alkyl and $C_1$ to $C_4$ alkoxy group: a substituted phenyl group having 1 to 3 substituents selected from the group consisting of an acetoxy group, a halogen atom, hydroxyl group and a nitro group, when R is selected from the group consisting of an alkoxy group, a hydroxyl group, an amino group and a substituted amino group having a substituent selected from the group consisting of a $C_1$ to $C_5$ monalkyl group, a $C_1$ to $C_5$ dialkyl group, a cyclohexyl amino group, a dicyclohexyl amino group, a piperidino group and a morpholino group;

and A is a phenyl group when R is selected from the group consisting of a methoxy group, an amino group and a substituted amino group having a substituent selected from the group consisting of a $C_1$ to $C_5$ monoalkyl group, a $C_1$ to $C_5$ dialkyl group, a cyclohexyl amino group, a dicyclohexyl amino group, a piperidino group and a morpholino group; and a pharmaceutically acceptable salt thereof.

2. The compound of claim 1 wherein the phenyl group is substituted with one member selected from 2-methyl; 3-methyl; 4-methyl; 2,5-dimethyl; 2,6-dimethyl; 3,4-dimethyl; 2,3,4-trimethyl; 2,3,4,5,6-pentamethyl; 4-ethyl; 4-n-butyl; 4-tert-butyl; 2-methoxy; 4-methoxy; 2,3-dimethoxy; 4-acetoxy; 2-fluoro; 3-fluoro; 4-fluoro; 2-chloro; 3-chloro; 4-chloro; 4-bromo; 3-chloro-4-methoxy; 4-methoxy-3,5-dichloro; 4-hydroxy; 2-nitro and 4-nitro groups.

3. The compound of claim 1 wherein the alkoxy group is selected from methoxy, ethoxy, n-propoxy, iso-propoxy, n-butoxy, t-butoxy and n-hexloxy groups.

4. The compound of claim 1 wherein the substituted amino group is selected from methylamino, ethylamino, butylamino, cyclohexylamino, diethylamino, dimethylamino, dicyclohexylamino, piperidino and morpholino groups.

5. The compound of claim 1 in the form of a pharmaceutically acceptable salt.

6. The salt of claim 5 formed with one member selected from sodium, potassium, lithium, barium, calcium, ammonium, lysine, triethylamine and dimethylamine.

7. A compound selected from the group consisting of
N-(4-methylbenzylthiocarbonyl)-L-phenylalanine,
N-(4-methylbenzylthiocarbonyl)-L-phenylalanine methylester,
N-(4-methylbenzylthiocarbonyl)-L-phenylalanine amide,
N-(4-methylbenzylthiocarbonyl)-L-phenylalanine ethylamide,
N-(4-chlorobenzylthiocarbonyl)-L-phenylalanine, N-(4-chlorobenzylthiocarbonyl)-L-phenylalanine ethylamide,
N-(4-chlorobenzylthiocarbonyl)-L-phenylalanyl-L-phenylalanine methylester,
N-(4-methoxybenzylthiocarbonyl)-L-phenylalanine methylester,
N-(4-nitrobenzylthiocarbonyl)-L-phenylalanine methylester,
N-benzothiocarbonyl-DL-phenylalanine methylester,
N-(3-methylbenzylthiocarbonyl)-L-phenylalanine methylester,
N-(2,6-dimethylbenzylthiocarbonyl)-L-phenylalanine,
N-(2,6-dimethylbenzylthiocarbonyl)-L-phenylalanine methylester,
N-(2,5-dimethylbenzylthiocarbonyl)-L-phenylalanine,
N-(2,5-diemthylbenzylthiocarbonyl)-L-phenylalanine methylester,
N-(4-tert-butylbenzylthiocarbonyl)-L-phenylalanine,
N-(2,3,4,5,6-pentamethylbenzylthiocarbonyl)-L-phenylalanine,
N-(2,3,4,5,6-pentamethylbenzylthiocarbonyl)-L-phenylalanine methyester,
N-(α-naphtylmethylthiocarbonyl)-L-phenylalanine,
N-(α-naphtylbenzylthiocarbonyl)-L-phenylalanine methylester,
N-(4-methylbenzylthiocarbonyl)-D-phenylalanine,
N-(4-methylbenzylthiocarbonyl)-DL-phenylalanine,
N-(4-acetoxybenzylthiocarbonyl)-L-phenylalanine and
N-(4-hydroxybenzylthiocarbonyl)-L-phenylalanine methylester.

8. A pharmaceutical composition comprising a pharmaceutical carrier or excipient and as active ingredient, an effective amount of a compound of the formula:

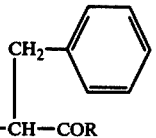

$$A-CH_2-SCONH-CH-COR \quad [I]$$

wherein A is selected from the group consisting of a phenyl group; a substituted phenyl group having 1 to 5 substituents selected from the group consisting of a $C_1$ to $C_5$ alkyl and an acetoxy; a substituted phenyl group having 1 to 3 substituents selected from the group consisting of a $C_1$ to $C_6$ alkoxy group, a halogen atom, hydroxy group, a nitro group and a naphthyl group; and R is selected from the group consisting of a hydroxy group, an alkoxy group, an amino group, and a substituted amino group having a substituent selected from the group consisting of a $C_1$ to $C_5$ monalkyo group, a $C_1$ to $C_5$ dialkyl group, a cyclohexylamino group, a dicyclohexylamino group, a piperidino group and a morpholino group; and a pharmaceutically acceptable salt thereof.

9. The composition of claim 8 wherein the phenyl group is substituted with one member selected from 2-methyl; 3-methyl; 4-methyl; 2,5-diemthyl; 2,6-dimethyl; 3,4-dimethyl; 2,3,4-trimethyl; 2,3,4,5,6-pentamethyl; 4-ethyl; 4-n-butyl; 4-tert-butyl; 2-methoxy; 4-methoxy; 2,3-dimethoxy; 4-acetoxy; 2-fluoro, 3-fluoro; 4-fluoro; 4-bromo; 2-chloro; 3-chloro; 4-chloro; 3-chloro-4-methoxy; 4-methoxy-3,5-dichloro; 4-hydroxy, 2-nitro and 4-nitro groups.

10. The composition of claim 8 wherien the alkoxy group is selected from methoxy, ethoxy, n-propoxy, iso-propoxy, n-butoxy, tert-butoxy and n-hexyloxy groups.

11. The composition of claim 8 wherein the substituted amino group is selected from methylamino, ethylamino, butylamino, cyclohexylamino, dimethylamino, diethylamino, dicyclohexylamino, piperidino and morpholino groups.

12. The composition of claim 8 wherein the salt is formed with one member selected from sodium, potassium, lithium, barium, ammonium, calcium, lysine, triethylamine and dimethylamine.

13. A process for lowering lipids in an animal subject which comprises administering to said subject an effective amount of the composition defined in claim 8.

14. The process of claim 13 wherein said composition is administered to a human subject in an amount of 0.5 to 3 gr. per day of active compound per 50 to 60 kg. bodily weight.

15. The process of claim 13 wherein said composition is administered orally in the form of a tablet, capsule or powder.

* * * * *